United States Patent
Giesing et al.

(10) Patent No.: US 10,792,297 B2
(45) Date of Patent: Oct. 6, 2020

(54) METHODS OF TREATMENT AND MAINTENANCE THERAPY FOR BLADDER CANCER USING GEMCITABINE

(71) Applicant: Taris Biomedical LLC, Lexington, MA (US)

(72) Inventors: Dennis Giesing, Lee's Summit, MO (US); Christopher Cutie, Lexington, MA (US)

(73) Assignee: TARIS Biomedical LLC, Lexington, MA (US)

( * ) Notice: Subject to any disclaimer, the term of this patent is extended or adjusted under 35 U.S.C. 154(b) by 0 days.

(21) Appl. No.: 16/183,673

(22) Filed: Nov. 7, 2018

(65) Prior Publication Data

US 2019/0175637 A1    Jun. 13, 2019

Related U.S. Application Data

(60) Provisional application No. 62/583,394, filed on Nov. 8, 2017.

(51) Int. Cl.

| | | |
|---|---|---|
| *A61K 31/7068* | (2006.01) | |
| *A61P 13/10* | (2006.01) | |
| *C07H 19/06* | (2006.01) | |
| *A61P 31/04* | (2006.01) | |
| *A61K 9/00* | (2006.01) | |
| *A61P 35/00* | (2006.01) | |
| *A61K 9/06* | (2006.01) | |
| *A61K 47/36* | (2006.01) | |

(52) U.S. Cl.
CPC ........ *A61K 31/7068* (2013.01); *A61K 9/0034* (2013.01); *A61K 9/06* (2013.01); *A61K 47/36* (2013.01); *A61P 13/10* (2018.01); *A61P 31/04* (2018.01); *A61P 35/00* (2018.01); *C07H 19/06* (2013.01)

(58) Field of Classification Search
None
See application file for complete search history.

(56) References Cited

U.S. PATENT DOCUMENTS

| | | |
|---|---|---|
| 8,343,516 B2 | 1/2013 | Daniel et al. |
| 8,679,094 B2 | 3/2014 | Cima et al. |
| 9,107,816 B2 | 8/2015 | Lee et al. |
| 9,636,448 B2 | 5/2017 | Giesing |
| 10,543,346 B2 | 1/2020 | Giesing |
| 2012/0203203 A1 | 8/2012 | Lee et al. |
| 2013/0158675 A1 | 6/2013 | Hutchins, III et al. |
| 2014/0056986 A1 | 2/2014 | Desai |
| 2014/0221981 A1 | 8/2014 | Cima |
| 2014/0276636 A1 | 9/2014 | Lee et al. |
| 2015/0165177 A1 | 6/2015 | Giesing |
| 2015/0165178 A1 | 6/2015 | Giesing |
| 2015/0216937 A1 | 8/2015 | Wen |
| 2015/0250717 A1 | 9/2015 | Giesing et al. |
| 2015/0360012 A1 | 12/2015 | Sansone et al. |
| 2016/0008271 A1 | 1/2016 | Lee |
| 2016/0199544 A1 | 7/2016 | Lee et al. |
| 2016/0310715 A1 | 10/2016 | Lee |
| 2019/0060344 A1 | 2/2019 | Giesing |
| 2019/0388338 A1 | 12/2019 | Giesing |
| 2020/0060966 A1 | 2/2020 | Giesing |

FOREIGN PATENT DOCUMENTS

| | | |
|---|---|---|
| WO | WO-2011/031855 A2 | 3/2011 |
| WO | WO-2011/031855 A3 | 3/2011 |
| WO | WO2014036556 A2 | 3/2014 |
| WO | WO2014036556 A3 | 4/2014 |
| WO | WO-2014/144066 A1 | 9/2014 |
| WO | WO-2014/145638 A1 | 9/2014 |
| WO | WO-2015/026813 A1 | 2/2015 |
| WO | WO2015134911 A1 | 9/2015 |
| WO | WO-2015/200752 A1 | 12/2015 |
| WO | WO2017193098 A1 | 11/2017 |
| WO | WO2019023388 A1 | 1/2019 |
| WO | WO2020028554 A1 | 2/2020 |

OTHER PUBLICATIONS

Lorenzo et al., "Gemcitabine Versus Bacille Calmette-Guerin After Initial Bacille Calmette-Gue´rin Failure in Non-Muscle-Invasive Bladder Cancer" Cancer vol. 116 pp. 1893-1900 (Year: 2010).*
Yuh et al., "Pooled Analysis of Clinical Outcomes with Neoadjuvant Cisplatin and Gemcitabine Chemotherapy for Muscle Invasive Bladder Cancer" Journal of Urology vol. 189 pp. 1682-1686 (Year: 2013).*
Mertens et al., "Carboplatin Based Induction Chemotherapy for Nonorgan Confined Bladder Cancer—A Reasonable Alternative for Cisplatin Unfit Patients?" Journal of Urology vol. 188 pp. 1108-1114 (Year: 2012).*
Bidnur, S. et al. (Jan. 7, 2016). "Inhibiting Immune Checkpoints for the Treatment of Bladder Cancer," *Bladder Cancer* 2(1):15-25.
clinicaltrials.gov. NCT02720367. (Mar. 21, 2016; updated Apr. 19, 2018). "Safety and Tolerability of TAR-200 mg in Subjects With Non-Muscle-Invasive Bladder Cancer," located at <https://clinicaltrials.gov/ct2/history/NCT02720367?A=6&B=6&C=merged>, last visited on Feb. 21, 2019, 14 pages.
clinicaltrials.gov. NCT02722538. (Mar. 30, 2016; last updated Mar. 6, 2018). "Safety and Tolerability of GemRIS 225 mg in Subjects With Muscle-Invasive Bladder Cancer," located at <https://clinicaltrials.gov/ct2/history/NCT02722538?A=1&B=10&C=merged >, last visited on Feb. 21, 2019, 20 pages.
clinicaltrials.gov. NCT03404791. (Jan. 19, 2018). "Safety and Tolerability of TAR-200 in Subjects With Muscle-Invasive Bladder Cancer Who Are Unfit for Radical Cystectomy," located at < https://www.clinicaltrials.gov/ct2/history/NCT03404791?V_1=View >, last visited on Feb. 21, 2019, 15 pages.

(Continued)

*Primary Examiner* — Eric Olson
(74) *Attorney, Agent, or Firm* — Morrison & Foerster LLP

(57) ABSTRACT

Provided are methods of treating urothelial carcinomas of the lower tract comprising administering comprising administering gemcitabine continuously and locally to the bladder of an individual in an induction therapy and/or maintenance therapy.

25 Claims, 1 Drawing Sheet

(56) References Cited

OTHER PUBLICATIONS

Cockerill, P.A. et al. (Mar. 2016; e-pub May 2, 2015.). "Intravesical Gemcitabine in Combination with Mitomycin C as Salvage Treatment in Recurrent Non-Muscle-Invasive Bladder Cancer," *BJU Int.* 117(3):456-462.
Daneshmand, S. et al. (2017; e-pub. May 30, 2017). "Effect of GemRIS (Gemcitabine-Releasing Intravesical System, TAR-200) on Antitumor Activity in Muscle-Invasive Bladder Cancer (MIBC)," *Journal of Clinical Oncology* 35(15):suppl. e16000, located at, <http://ascopubs.org/doi/abs/10.1200/JCO.2017.35.15_suppl.e16000>, last visited on Feb. 21, 2019, 2 pages.
Leach, D.R. et al. (Mar. 22, 1996). "Enhancement of Antitumor Immunity by CTLA-4 Blockade," *Science* 271(5256):1734-1736.
Li, J. et al. (Oct. 2014). "Effect of Internal Iliac Artery Chemotherapy after Transurethral Resection of Bladder Tumor for Muscle Invasive Bladder Cancer," *Chin J Cancer Res.* 26(5):558-563.
Pardoll, D.M. (Apr. 2012; e-pub. Mar. 22, 2012). "The Blockade of Immune Checkpoints in Cancer Immunotherapy," *Nature Reviews Cancer* 12(4):252-264.
Shariat, S.F. et al. (May 2010). "Update on Intravesical Agents for Non-Muscle-Invasive Bladder Cancer," *Immunotherapy* 2(3):381-392, 19 pages.
Shelley, M.D. et al. (Feb. 2012). "Intravesical Gemcitabine Therapy for Non-Muscle Invasive Bladder Cancer (NMIBC): A Systematic Review," *BJU International* 109(4):496-505.
Skinner, E.C. et al. (Oct. 2013; e-pub. Apr. 15, 2013). "SWOG S0353: Phase II Trial of Intravesical Gemcitabine in Patients with Nonmuscle Invasive Bladder Cancer and Recurrence after 2 Prior Courses of Intravesical Bacillus Calmette-Guérin," *The Journal of Urology* 190(4):1200-1204, 11 pages.
Wolchok, J.D. et al. (2008). "The Mechanism of Anti-CTLA-4 Activity and the Negative Regulation of T-Cell Activation," *The Oncologist* 13(Suppl 4):2-9.

International Search Report and Written Opinion dated Jan. 25, 2019 for PCT Application No. PCT/US2018/059698 filed on Nov. 7, 2018, 11 pages.
International Preliminary Report on Patentability dated Nov. 15, 2018 for PCT Application No. PCT/US2017/031445 filed on May 5, 2017, 10 pages.
International Search Report and Written Opinion dated Jun. 16, 2017 for PCT Application No. PCT/US2017/031445 filed on May 5, 2017, 15 pages.
U.S. Appl. No. 16/099,179, filed Nov. 15, 2018 by Giesing et al. (Not submitted herewith pursuant to the waiver of 37 C.F.R. § 1.98(a)(2)(iii) issued by the Office on Sep. 21, 2004.).
"TARIS Biomedical Announces Positive Results from Ph1b Trial of TAR-200 (GemRIS™) in Patients with Muscle Invasive Bladder Cancer," retrieved from URL:https://www.businesswire.com/news/home/20170106005117/en/TARIS-Biomedical-Announces-Positive-Results-Ph1b-Trial, last visited Nov. 6, 2019), (Jan. 6, 2017), 3 pages.
Oh, K.S. et al. (Nov. 2, 2009). "Combined-Modality Therapy With Gemcitabine and Radiation Therapy as a Bladder Preservation Strategy: Long-Term Results of a Phase I Trial," International Journal of Radiation: Oncology Biology Physics 74(2):511-517.
Stadler, W.M. et al. (Nov. 1997), "Phase II Study of Single-Agent Gemcitabine in Previously Untreated Patients With Metastatic Urothelial Cancer," J. of Clinical Oncology 15(11):3394-3398.
Sternberg, I.A. et al. (Nov. 2013). "Intravesical Gemcitabine for High Risk, Nonmuscle Invasive Balder Cancer After Bacillus Calmette-Guerin Treatment Failure," Journal of Urology 190(5):1686-1691.
Vogelzang, N.J. et al. (1999). "Gemcitabine and Other New Chemotherapeutic Agents for the Treatment of Metastatic Bladder Cancer," Urology 53:243-250.
Breyer, B.N. et al. (2010). "Sequential Intravesical Gemcitabine and Mitomycin C Chemotherapy Regimen in Patients With Non-Muscle Invasive Bladder Cancer," Urol. Oncol. 28(5):510-514. 9 pages.
Dall'Era, M.A. et al. (Jul. 2012). "Contemporary Management of Muscle-Invasive Bladder Cancer," Expert Rev. Anticancer Ther. 12(7):941-950, 18 pages.

\* cited by examiner

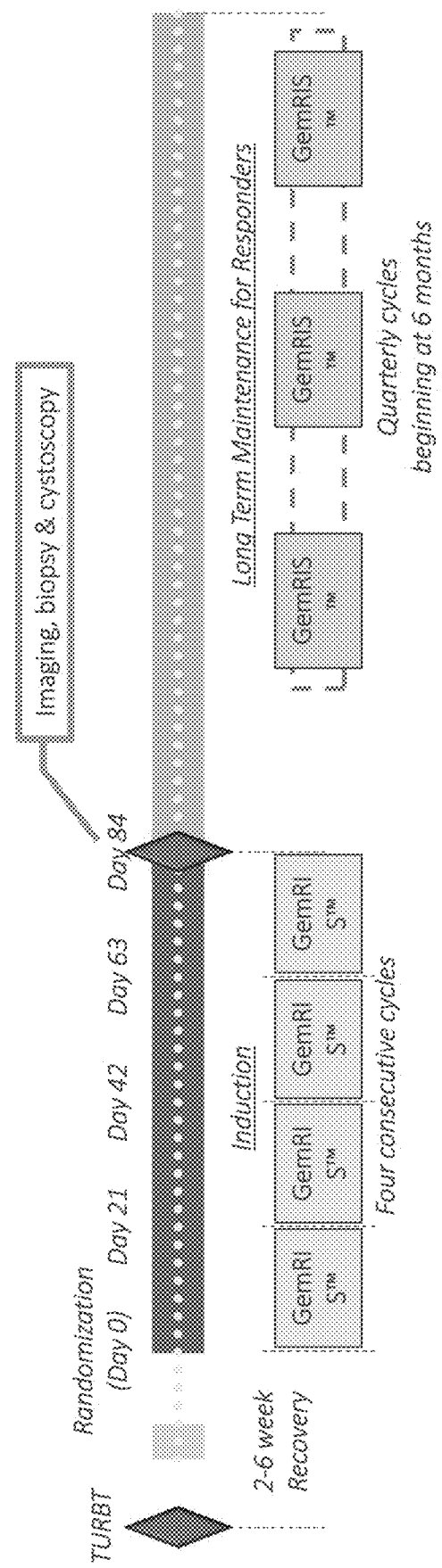

US 10,792,297 B2

METHODS OF TREATMENT AND MAINTENANCE THERAPY FOR BLADDER CANCER USING GEMCITABINE

RELATED APPLICATIONS

This application claims priority benefit to U.S. Provisional Application 62/583,394, filed on Nov. 8, 2017, which is incorporated by reference in its entirety for all purposes.

BACKGROUND OF THE INVENTION

Bladder cancer is a significant medical problem, and currently available treatment options are unsatisfactory for a number of reasons. In general, bladder cancers are classified as muscle invasive bladder cancer (MIBC) or non-muscle invasive bladder cancer (NMIBC). The pathological classification and staging of bladder cancer is as follows: pTa (urothelial involvement); pTis (high risk urothelial confined); pT1 (lamina propria invasion); pT2 (muscularis invasion); pT3 (perivesical fat invasion); and pT4 (pelvic organ extension). Bladder cancers can also be classified by grade as Grade 1/3 (well differentiated); Grade 2/3 (moderately differentiated); Grade 3/3 (poorly differentiated). In addition, bladder cancers can be classified by stage as Stages 0-IV (designating the extent the cancer invades the bladder wall, with Stage 0 restricted to the urothelium and Stage IV describing cancer that has penetrated the full thickness of the bladder wall invading adjacent organs or tissues). Most bladder cancers are transitional cell carcinomas of epithelial origin and classified as non-muscle invasive cancer (NMIBC) confined to the inner lining of the bladder. At initial presentation, most bladder cancers are superficial NMIBCs and include stages pTa, pTis and pT1 disease. MIBC include stages pT2, pT3 and pT4.

For patients with locally advanced muscle-invasive bladder cancer (MIBC), radical cystectomy is the standard treatment, with chemotherapy administered either before surgery or after surgery (American Cancer Society, 2016b). The National Comprehensive Cancer Network (NCCN) and the European Association of Urology (EAU) have also recommended RC, along with radiotherapy and chemotherapy (if possible) as potential curative, primary treatments for patients with MIBC (NCCN, 2017; Gakis, 2013). For patients who are not candidates for potentially curative treatments, palliative radiotherapy alone or transurethral resection of bladder tumors (TURBT) alone is recommended.

Patients who are unfit for definitive treatment with curative intent undergo repetitive or debulking, palliative TURBT to attempt to limit local advancement of untreated and undertreated disease. These non-curative strategies are also employed to attempt to mitigate the worsening of morbid symptoms caused by invasive tumors which often include bleeding, obstruction and pain often resulting in repeated emergency treatments.

Published Applications US2012/0203203, US2013/0158675, US2015/0360012, US2015/0165177, US2015/0165178, US2016/0199544, WO2014/145638, WO2015/200752, WO2011/031855 are hereby incorporated by reference in their entirety. All other references disclosed herein are incorporated by reference in their entirety.

BRIEF SUMMARY OF THE INVENTION

In some embodiments, provided herein is a method of providing maintenance therapy for an individual, wherein the maintenance therapy follows at least one previous therapy, wherein the maintenance therapy comprises administering gemcitabine continuously to the individual one, two or more times during one, two or more delivery periods wherein the gemcitabine is delivered locally to the bladder of the individual, wherein each delivery period is at least one week, wherein there is a rest period between each delivery period of at least one week (e.g., at least one month), and wherein the individual has a urothelial carcinoma of the lower tract.

In some embodiments, provided herein is a method of treating a urothelial carcinoma of the lower tract in an individual comprising a) administering to the individual continuously an effective amount of gemcitabine during an induction phase; and b) administering to the individual continuously an effective amount of gemcitabine during a maintenance phase, wherein the gemcitabine is delivered locally to the bladder of the individual, wherein the induction phase and maintenance phases are separated by a rest period, and wherein the induction phase is about 12 weeks.

Also provided herein is a method of bladder preservation in an individual comprising a) administering to the individual continuously an effective amount of gemcitabine during an induction phase; and b) administering to the individual continuously an effective amount of gemcitabine during a maintenance phase, wherein the gemcitabine is delivered locally to the bladder of the individual, wherein the induction phase and maintenance phases are separated by a rest period, wherein the induction phase is about 12 weeks, and wherein the individual has a urothelial carcinoma of the lower tract.

In some embodiments, the gemcitabine is delivered into the bladder by an intravesicular device. In some embodiments, the intravesicular device contains about 225 mg gemcitabine.

In some embodiments, the delivery periods are each 3 weeks. In some embodiments, the rest period is about 0-3 months (e.g., 3 months).

In some embodiments, gemcitabine is delivered at a dose from about 1 mg/day to about 300 mg/day during the delivery periods. In some embodiments, the concentration of gemcitabine in the urine is from about 1 µg/mL to about 90 µg/mL during the delivery periods. In some embodiments, the average concentration of gemcitabine in the urine is about 5 to 20 µg/mL during the delivery periods.

In some embodiments, the individual is ineligible for or has refused cisplatin-based chemotherapy.

In some embodiments, the individual is unfit for, ineligible for, or has refused a radical cystectomy.

In some embodiments, the individual has muscle invasive bladder cancer.

In some embodiments, the individual has non-muscle invasive bladder cancer.

In some embodiments, the rest period between the induction phase and the maintenance phase is about 1-3 months.

In some embodiments, the maintenance phase comprises two or more gemcitabine delivery periods. In some embodiments, gemcitabine delivery periods during maintenance phase (also referred to as "the maintenance phase gemcitabine delivery periods") are each separated by a rest period of about 1-3 months.

In some embodiments, the maintenance phase gemcitabine delivery periods are each 1-3 weeks.

BRIEF DESCRIPTION OF DRAWINGS

FIG. 1 illustrates the study protocol as described in Example 1.

DETAILED DESCRIPTION OF THE INVENTION

Provided herein are methods of treating urothelial carcinomas of the lower tract comprising administering gemcitabine locally to the bladder a maintenance therapy. Also provided herein are methods of treating urothelial carcinomas of the lower tract comprising administering gemcitabine locally to the bladder an effective amount of gemcitabine during an induction phase and/or an effective amount of gemcitabine during an maintenance phase. In some embodiments, the induction phase comprises more than one delivery periods, such as about two, three, four, five or more delivery periods. In some embodiments, the delivery periods during the induction phase are consecutive. In some embodiments, no rest period or minimum rest period (such as a rest period less than a week) is between the consecutive delivery periods during the induction phase. In some embodiments, the induction phase comprises about four delivery period (e.g., four consecutive delivery periods), wherein each delivery period is about 3 weeks (such as 18-24 days). In some embodiments, the maintenance phase comprises one or more delivery period. In some embodiments, each delivery period during the maintenance period is about three weeks (such as about 18-24 days). In some embodiments, there is a rest period between delivery periods during maintenance phase is about two months (e.g., about 65-75 days). In some embodiments, the urothelial carcinoma is a bladder cancer. In some embodiments, the bladder cancer is muscle-invasive bladder cancer. In some embodiments, the bladder cancer is an organ-confined muscle-invasive bladder cancer (such as non-metastatic MIBC (i.e., M0 MIBC), such as M0 N0 MIBC). In some embodiments, the bladder cancer is a T2 or T3 bladder cancer. In some embodiments, the bladder cancer is about T2 or T3 M0 bladder cancer (such as T2 or T3 M0 N0 MIBC).

While radical cystectomy (RC) remains the standard treatment for MIBC (such as organ-confined (OC) MIBC), the natural history of patients unable to receive curative intent therapy (CIT) is not well understood. Inability to receive CIT is typically due to a patient's underlying comorbidities, frailty, and/or age. Although a substantial proportion of these patients are diagnosed with clinical stage T2-T3 M0 (OC) disease, they do not receive CIT and ultimately die of their disease. In an analysis of patients who were diagnosed with T2-T4 MIBC between 1997 and 2014 in Sweden and did not receive a curative intent therapy (such as radical cystectomy), it was found that this patient population experienced a substantial disease-specific morbidity, were hospitalized frequently over their final year of life, and died primarily from bladder cancer progression. The present application provides methods for treating urothelial carcinomas of the lower tract (such as bladder cancer, such as MIBC, such as organ-confined MIBC) that have shown advantageous effects on patients, especially the patient population that is unfit for, is ineligible, or unwilling to receive a curative intent therapy such as radical cystectomy. For example, the present application demonstrates that frail patients such as older patients who are unfit, ineligible or unwilling to receive radical cystectomy can well tolerate an induction therapy that comprises four consecutive delivery periods of gemcitabine and each delivery period is about 3 weeks (such as 18-24 days). The present application shows that these patients have achieved 50% complete response and 80% objective response rate on a per protocol basis. It is also demonstrated that the provided methods are able to effectively improve symptoms associated with the bladder cancer and/or previous or present treatment of bladder cancer, such as reducing frequencies of hematuria, alleviating pain, etc. Most strikingly, it is shown that the provided methods exhibit a durable effect for at least about 100 days after the induction therapy, thus providing a basis for effective maintenance therapy as discussed herein.

I. Methods of the Present Invention

Provided herein are methods of treating a ureothial carcinoma of the lower tract by administering gemcitabine locally to the bladder multiple times over a period of several months. Such methods are useful as maintenance therapy, for example to prevent recurrence, and in bladder sparing protocols.

The term "continuous" or "continuously" as used herein refers to sustained administration of gemcitabine over a period of time.

The term "individual" as used herein refers to a mammal, including humans. An individual includes, but is not limited to, human, bovine, horse, feline, canine, rodent, or primate. In some embodiments, the individual is human.

Reference to "about" a value or parameter herein includes (and describes) embodiments that are directed to that value or parameter per se. For example, "about 21 days" includes 21 days.

The term "about X-Y" used herein has the same meaning as "about X to about Y."

The term "effective amount" used herein refers to an amount of a compound or composition sufficient to treat a specified disorder, condition or disease such as ameliorate, palliate, lessen, and/or delay one or more of its symptoms. In reference to cancers or other unwanted cell proliferation, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay occurrence and/or recurrence. An effective amount can be administered in one or more administrations, in the case of cancer, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

In some embodiments, the methods provided herein are useful for improving the quality of life of a patient. For example, the methods provided herein can be used to provide chronic treatment for patients who are unable to undergo cystectomy. In some embodiments, the methods provided herein can be used as a palliative care. In some embodiments, provided herein is a method of reducing pain in an individual having cancer.

Dosage Regimens

The following section describes various aspects (embodiments) of dosing and treatment regions, any and all of which apply to the methods described herein.

In some embodiments, provided herein is a method of maintenance therapy following at least one previous therapy for an individual, comprising administering gemcitabine continuously and locally to the bladder of the individual during a delivery period. In some embodiments, provided herein is a method of providing maintenance therapy for an individual, wherein the maintenance therapy follows at least one previous therapy, wherein the maintenance therapy comprises administering gemcitabine continuously to the individual two or more times during two or more delivery periods, wherein the each delivery period is separated by a rest period of about or at least about 1 month. In some embodiments, the rest period is about or at least about 1 to 12 months, for example, at least about 1 month, about 2 months, about 3 months, about 4 months, about 5 months, about 6 months or about one year. In some embodiments, the rest period is about 3 months. In some embodiments, the rest period is about 65-75 days, for example, 68 to 72 days. In some embodiments, provided herein is a method of maintenance therapy following at least one previous therapy for an individual, comprising administering gemcitabine continuously and locally to the bladder of the individual two or more times during two or more consecutive delivery periods. In some embodiments, there is a rest period of about 0-12 months after the two or more consecutive delivery period. In some embodiments, there is a rest period of about 0-12 months after the two or more consecutive delivery period. In some embodiments, the individual has a cT2 or cT3 bladder cancer (such as cT2 or cT3 MIBC). In some embodiments, the individual has an organ-confined muscle-invasive bladder cancer (such as non-metastatic MIBC (i.e., M0 MIBC), such as M0 N0 MIBC). In some embodiments, the individual has a cT2 or cT3 M0 MIBC (e.g., cT2 or cT3 N0 M0 MIBC). In some embodiments, the individual is responsive (such as having a complete response, partial response and/or stable disease) to the at least one previous therapy, wherein the at least one previous therapy comprises administering gemcitabine continuously and/or locally (e.g., to the bladder of the individual) to the individual. In some embodiments, there is a rest period between the previous therapy and the maintenance therapy. In some embodiments, the rest period between the previous therapy and the maintenance therapy is about or at least about 1 to 12 months, for example, at least about 1 month, about 2 months, about 3 months, about 4 months, about 5 months, about 6 months or about one year. In some embodiments, the rest period between the previous therapy and the maintenance therapy is about or at least about 3 months. In some embodiments, the individual is responsive (e.g., having a complete response, partial response, and/or stable disease) to the at least one previous therapy. In some embodiments, the individual is selected for maintenance therapy when the individual has a complete response to the at least one previous therapy. In some embodiments, the previous response comprises at least one induction phase therapy comprising administering gemcitabine continuously and locally to the bladder of the individual for at least a week (e.g., 12 weeks).

In some embodiments, provided herein is a method of providing maintenance therapy for an individual, wherein the maintenance therapy follows at least one previous therapy, wherein the maintenance therapy comprises administering gemcitabine continuously to the individual two or more times during two or more delivery periods, wherein each delivery period is separated by a rest period of at least 1 month, and wherein each delivery period is at least 1 week. In some embodiments, each delivery period is about 1 week, 2 weeks, or 3 weeks. In some embodiments, each delivery period is about 3 weeks (such as 18-24 days). In some embodiments, the individual has a cT2 or cT3 bladder cancer (such as cT2 or cT3 MIBC). In some embodiments, the individual has an organ-confined muscle-invasive bladder cancer (such as non-metastatic MIBC (i.e., M0 MIBC), such as M0 N0 MIBC). In some embodiments, the individual has a cT2 or cT3 M0 MIBC (e.g., cT2 or cT3 N0 M0 MIBC). In some embodiments, the individual is responsive (such as having a complete response, partial response and/or stable disease) to the at least one previous therapy, wherein the at least one previous therapy comprises administering gemcitabine continuously and/or locally to the individual (e.g., to the bladder of the individual). In some embodiments, the individual is responsive (e.g., having a complete response, partial response, and/or stable disease) to the at least one previous therapy. In some embodiments, the individual is selected for maintenance therapy when the individual has a complete response to the at least one previous therapy. In some embodiments, the previous response comprises at least one induction phase therapy comprising administering gemcitabine continuously and locally to the bladder of the individual for at least a week (e.g., 12 weeks).

In some embodiments, provided herein is a method of providing maintenance therapy for an individual, wherein the maintenance therapy follows at least one previous therapy, wherein the maintenance therapy comprises administering gemcitabine continuously to the individual two or more times during two or more delivery periods, wherein the each delivery period is separated by a rest period of at least 1 month, and wherein each delivery period is at least 1 week, and wherein the gemcitabine is delivered locally to the bladder by an intravesicular device. In some embodiments the device comprises about 225 mg gemcitabine. In some embodiments, the delivery periods are separated by a rest period of about 2 months, about 3 months, about 4 months, about 5 months, or about 6 months. In some embodiments, the rest period is about 3 months. In some embodiments, the individual has a cT2 or cT3 bladder cancer (such as cT2 or cT3 MIBC). In some embodiments, the individual has an organ-confined muscle-invasive bladder cancer (such as non-metastatic MIBC (i.e., M0 MIBC), such as M0 N0 MIBC). In some embodiments, the individual has a cT2 or cT3 M0 MIBC (e.g., cT2 or cT3 N0 M0 MIBC). In some embodiments, the individual is responsive (such as having a complete response, partial response and/or stable disease) to the at least one previous therapy, wherein the at least one previous therapy comprises administering gemcitabine continuously and/or locally to the individual (e.g., to the bladder of the individual). In some embodiments, the individual is responsive (e.g., having a complete response, partial response, and/or stable disease) to the at least one previous therapy. In some embodiments, the individual is selected for maintenance therapy when the individual has a complete response to the at least one previous therapy. In some embodiments, the previous response comprises at least one induction phase therapy comprising administering gemcitabine continuously and locally to the bladder of the individual for at least a week (e.g., 12 weeks).

In some embodiments, the maintenance therapy comprises administering about 225 mg of gemcitabine about every 3 months twice. In some embodiments, the method comprises administering about 225 mg of gemcitabine about every 3 months 3 times, 4 times, 5 times, 6 times, 7 times, or for the lifetime of the individual. In some embodiments, the individual has a cT2 or cT3 bladder cancer (such as cT2 or cT3 MIBC). In some embodiments, the individual has an organ-confined muscle-invasive bladder cancer (such as non-metastatic MIBC (i.e., M0 MIBC), such as M0 N0 MIBC). In some embodiments, the individual has a cT2 or cT3 M0 MIBC (e.g., cT2 or cT3 N0 M0 MIBC). In some embodiments, the individual is responsive (such as having a complete response, partial response and/or stable disease) to a previous therapy, wherein the previous therapy comprises administering gemcitabine continuously and/or locally to the individual (e.g., to the bladder of the individual).

In some embodiments, the maintenance therapy comprises administering about 225 mg of gemcitabine to an individual about every 2 months for about 1 year, wherein the gemcitabine is delivered locally to the bladder. In some embodiments, about 225 mg of gemcitabine is administered to an individual about every 3 months for about 1 year. In some embodiments, about 225 mg of gemcitabine is administered to the individual about every 4 months for about 1 year. In some embodiments about 225 mg of gemcitabine is administered to the individual about every 5 months for about 1 year. In some embodiments about 225 mg of gemcitabine is administered to the individual every 6 months. In some embodiments, the individual has muscle invasive bladder cancer. In some embodiments, the individual has non-muscle invasive bladder cancer. In some embodiments, the individual is ineligible or has refused cisplatin based chemotherapy. In some embodiments, the individual is unfit for, is ineligible, or has refused a radical cystectomy. In some embodiments, the individual has a cT2 or cT3 bladder cancer (such as cT2 or cT3 MIBC). In some embodiments, the individual has an organ-confined muscle-invasive bladder cancer (such as non-metastatic MIBC (i.e., M0 MIBC), such as M0 N0 MIBC). In some embodiments, the individual has a cT2 or cT3 M0 MIBC (e.g., cT2 or cT3 N0 M0 MIBC). In some embodiments, the individual is responsive (such as having a complete response, partial response and/or stable disease) to a previous therapy, wherein the previous therapy comprises administering gemcitabine continuously and/or locally to the individual (e.g., to the bladder of the individual).

In some embodiments, a gemcitabine releasing device comprising about 225 mg gemcitabine is placed into the bladder of an individual for at least 1 week about every 3 months for about 1 year. In some embodiments a gemcitabine releasing device comprising about 225 mg gemcitabine is placed into the bladder of an individual for 2 weeks about every 3 months for about 1 year. In some embodiments the gemcitabine releasing device comprising about 225 mg gemcitabine is placed into the bladder of an individual for 3 weeks about every 3 months for about 1 year. In some embodiments a gemcitabine releasing device comprising about 225 mg gemcitabine is placed into the bladder of an individual for 3 weeks about every 3 months for the lifetime of the individual. In some embodiments, the individual has a cT2 or cT3 bladder cancer (such as cT2 or cT3 MIBC). In some embodiments, the individual has an organ-confined muscle-invasive bladder cancer (such as non-metastatic MIBC (i.e., M0 MIBC), such as M0 N0 MIBC). In some embodiments, the individual has a cT2 or cT3 M0 MIBC (e.g., cT2 or cT3 N0 M0 MIBC). In some embodiments, the individual is responsive (such as having a complete response, partial response and/or stable disease) to a previous therapy, wherein the previous therapy comprises administering gemcitabine continuously and/or locally to the individual (e.g., to the bladder of the individual).

In some embodiments, the method comprises (i) placing a first gemcitabine releasing intravesicular (intravesical) device into the bladder of the individual, wherein the first gemcitabine releasing intravesicular (intravesical) device remains in the bladder, wherein the first gemcitabine releasing intravesicular (intravesical) device contains about 225 mg of gemcitabine, (ii) removing the first gemcitabine releasing intravesicular (intravesical) device after about 3 weeks (such as 18-24 days), (iii) placing a second gemcitabine releasing device into the bladder of the individual about 3 months after the first gemcitabine releasing intravesicular (intravesical) device is placed in the bladder, wherein the second gemcitabine releasing intravesicular (intravesical) device remains in the bladder for 3 weeks, wherein the second gemcitabine releasing intravesicular (intravesical) device contains about 225 mg gemcitabine, (iv) removing the second gemcitabine releasing device. In some embodiments, steps i-iv are repeated about every 3 months for about 1 year, 2 years, 3 years, or for the lifetime of the individual. In some embodiments, the individual has muscle invasive bladder cancer. In some embodiments, the individual has non-muscle invasive bladder cancer. In some embodiments, the individual is ineligible for or has refused cisplatin based chemotherapy. In some embodiments, the individual is unfit for, is ineligible, or has refused a radical cystectomy. In some embodiments, the individual has a cT2 or cT3 bladder cancer (such as cT2 or cT3 MIBC). In some embodiments, the individual has an organ-confined muscle-invasive bladder cancer (such as non-metastatic MIBC (i.e., M0 MIBC), such as M0 N0 MIBC). In some embodiments, the individual has a cT2 or cT3 M0 MIBC (e.g., cT2 or cT3 N0 M0 MIBC). In some embodiments, the individual is responsive (such as having a complete response, partial response and/or stable disease) to a previous therapy, wherein the previous therapy comprises administering gemcitabine continuously and/or locally to the individual (e.g., to the bladder of the individual).

In some embodiments, provided herein is a method of providing maintenance therapy for an individual, wherein the maintenance therapy follows at least one previous therapy, wherein the maintenance therapy comprises administering gemcitabine continuously to the individual two or more times during two or more delivery periods wherein the gemcitabine is delivered locally to the bladder of the individual, wherein each delivery period is at least one week and wherein the gemcitabine is delivered at a dose of about 15 mg/day to 100 mg/day during the delivery periods. In some embodiments, the gemcitabine is delivered at a dose of about 5 mg/day to about 250 mg/day, about 10 mg/day to about 200 mg/day, about 15 mg/day to about 100 mg/day, or about 15 mg/day to about 50 mg/day. In some embodiments, the gemcitabine is delivered at a dose of about 1 mg/day, about 5 mg/day, about 10 mg/day, about 15 mg/day, about 20 mg/day, about 23 mg/day, about 25 mg/day, about 30 mg/day, about 35 mg/day, about 40 mg/day, about 45 mg/day, about 50 mg/day, about 55 mg/day, about 60 mg/day, about 75 mg/day, about 100 mg/day, about 125 mg/day, about 150 mg/day, about 200 mg/day, about 250 mg/day, or about 300 mg/day. In some embodiments, the rest period is about 3 months. In some embodiments, the individual is responsive (such as having a complete response, partial response and/or stable disease) to the at least one previous therapy, wherein the at least one previous therapy comprises administering gemcitabine continuously and/or locally to the individual (e.g., to the bladder of the individual). In some embodiments, the individual is responsive (e.g., having a complete response, partial response, and/or stable disease) to the at least one previous therapy. In some embodiments, the individual is selected for maintenance therapy when the individual has a complete response to the at least one previous therapy. In some embodiments, the previous response comprises at least one induction phase therapy comprising administering gemcitabine continuously and locally to the bladder of the individual for at least a week (e.g., 12 weeks).

In some embodiments, provided herein is a method of providing maintenance therapy for an individual, wherein the maintenance therapy follows at least one previous therapy, wherein the maintenance therapy comprises administering gemcitabine continuously to the individual two or more times during two or more delivery periods wherein the gemcitabine is delivered locally to the bladder of the individual, wherein each delivery period is at least one week and wherein the concentration of gemcitabine in the urine of the individual is from about 1 µg/mL to about 10 µg/mL during the delivery periods. In some embodiments, the concentration of gemcitabine in the urine during the delivery periods is from about 1.0 µg/mL to about 100 µg/mL, from about 5.0 µg/mL to about 90 µg/mL, from about 10 µg/mL to about 80 µg/mL, from about 20 µg/mL to about 70 µg/mL, or from about 30 µg/mL to about 50 µg/mL. In some embodiments, the concentration of gemcitabine in the urine is about 1.0 µg/mL, about 5 µg/mL, about 10 µg/mL, about 15 µg/mL, about 20 µg/mL, about 25 µg/mL, about 30 µg/mL, about 40 µg/mL, about 50 µg/mL, about 60 µg/mL, about 70 µg/mL, about 80 µg/mL, about 90 µg/mL, or about 100 µg/mL. In some embodiments, the rest period is about 3 months. In some embodiments, the individual has a cT2 or cT3 bladder cancer (such as cT2 or cT3 MIBC). In some embodiments, the individual has an organ-confined muscle-invasive bladder cancer (such as non-metastatic MIBC (i.e., M0 MIBC), such as M0 N0 MIBC). In some embodiments, the individual has a cT2 or cT3 M0 MIBC (e.g., cT2 or cT3 N0 M0 MIBC). In some embodiments, the rest period is about 3 months. In some embodiments, the individual is responsive (such as having a complete response, partial response and/or stable disease) to the at least one previous therapy, wherein the at least one previous therapy comprises administering gemcitabine continuously and/or locally to the individual (e.g., to the bladder of the individual). In some embodiments, the individual is responsive (e.g., having a complete response, partial response, and/or stable disease) to the at least one previous therapy. In some embodiments, the individual is selected for maintenance therapy when the individual has a complete response to the at least one previous therapy. In some embodiments, the previous response comprises at least one induction phase therapy comprising administering gemcitabine continuously and locally to the bladder of the individual for at least a week (e.g., 12 weeks).

In some embodiments, the previous therapy as described herein comprises an induction phase therapy comprising delivering gemcitabine continuously and locally to the bladder of the individual for about 12 week. In some embodiments, the delivery comprises four delivery periods (such as four consecutive delivery periods) and each delivery period is about 3 weeks (such as 18-24 days). In some embodiments, the concentration of gemcitabine in the urine of the individual is at least about 0.1 µg/mL (e.g. from about 0.1 µg/mL to about 90 µg/mL) during the delivery periods for at least about one to two weeks out of three weeks. In some embodiments, the average concentration of gemcitabine in the urine is about 5 to 20 µg/mL for at least about one to two weeks out of three weeks. In some embodiments, about 225 mg of gemcitabine is administered during each delivery period. In some embodiments, the previous therapy comprises two or more induction phase therapies. In some embodiments, the two or more induction phase therapies are consecutive (i.e., there is no rest period between the two or more induction phase therapies). In some embodiments, there is a rest period between the two or more induction phase therapies. In some embodiments, the rest period is about one month to a year. In some embodiments, the rest period is about or at least about one, two, or three months.

In some embodiments, provided herein is a method of treating muscle invasive bladder cancer in an individual who is unfit or not eligible for a cystectomy (such as radical cystectomy) comprising delivering gemcitabine continuously and locally to the bladder of the individual for about 12 week. In some embodiments, the individual is at least about 70 years old (such as at least about 70, 75, 80, 85, or 90 years old). In some embodiments, the individual has a compromised immune system. In some embodiments, the individual has a cT2 or cT3 organ-confined MIBC (e.g., N0 M0 MIBC). In some embodiments, the delivery comprises four delivery periods (such as four consecutive delivery periods) and each delivery period is about 3 weeks (such as 18-24 days). In some embodiments, the concentration of gemcitabine in the urine of the individual is at least about 0.1 µg/mL (e.g. from about 0.1 µg/mL to about 90 µg/mL) during the delivery periods for at least about one to two weeks out of three weeks. In some embodiments, the average concentration of gemcitabine in the urine is about 5 to 20 µg/mL for at least about one to two weeks out of three weeks. In some embodiments, about 225 mg of gemcitabine is administered during each delivery period. In some embodiments, the method further comprises a maintenance therapy that follows the delivery of gemcitabine for about 12 weeks. In some embodiments, there is a rest period between the delivery of gemcitabine and the maintenance therapy for about 12 weeks. In some embodiments, the rest period is at least about one, two, or three months. In some embodiments, the maintenance therapy comprises administering gemcitabine continuously and locally to the bladder of the individual about or at least about one, two or more times during one, two, or more delivery periods. In some embodiments, each delivery period in the maintenance phase is about or at least about one, two or three weeks. In some embodiments, the delivery period in the maintenance phase is about three weeks and the concentration of gemcitabine in the urine of the individual is at least about 0.1 µg/mL (e.g. from about 0.1 µg/mL to about 90 µg/mL) during the delivery periods for at least about one to two weeks out of three weeks. In some embodiments, about 225 mg of gemcitabine is administered during each delivery period during the maintenance phase.

In some embodiments, provided herein is a method of treating muscle invasive bladder cancer in an individual who is unfit or not eligible for a cystectomy (such as radical cystectomy) comprising at least two or more induction phase therapy, wherein each induction phase therapy comprises delivering gemcitabine continuously and locally to the bladder of the individual for about 12 week. In some embodiments, the individual is responsive to the first induction phase therapy, such as has a complete response, a partial response or stable disease. In some embodiments, the individual has a partial response or stable disease during or after the first or a prior induction phase therapy. In some embodiments, the individual is selected for the second induction phase therapy when the individual has a partial response or stable disease to the first or a prior induction phase therapy. In some embodiments, the individual is at least about 70 years old (such as at least about 70, 75, 80, 85, or 90 years old). In some embodiments, the individual has a compromised immune system. In some embodiments, the individual has a cT2 or cT3 organ-confined MIBC (e.g., N0 M0 MIBC). In some embodiments, the delivery comprises four delivery periods (such as four consecutive delivery periods) and each delivery period is about 3 weeks (such as 18-24 days). In some embodiments, the concentration of gemcitabine in the urine of the individual is at least about 0.1 µg/mL (e.g. from about 0.1 µg/mL to about 90 µg/mL) during the delivery periods for at least about one to two weeks out of three weeks. In some embodiments, the average concentration of gemcitabine in the urine is about 5 to 20 µg/mL for at least about one to two weeks out of three weeks. In some embodiments, about 225 mg of gemcitabine is administered during each delivery period. In some embodiments, the method further comprises a maintenance therapy that follows the delivery of gemcitabine for about 12 weeks. In some embodiments, there is a rest period between the delivery of gemcitabine and the maintenance therapy for about 12 weeks. In some embodiments, the rest period is at least about one, two, or three months. In some embodiments, the maintenance therapy comprises administering gemcitabine continuously and locally to the bladder of the individual about or at least about one, two or more times during one, two, or more delivery periods. In some embodiments, each delivery period in the maintenance phase is about or at least about one, two or three weeks. In some embodiments, the delivery period in the maintenance phase is about three weeks and the concentration of gemcitabine in the urine of the individual is at least about 0.1 µg/mL (e.g. from about 0.1 µg/mL to about 90 µg/mL) during the delivery periods for at least about one to two weeks out of three weeks. In some embodiments, about 225 mg of gemcitabine is administered during each delivery period during the maintenance phase.

In some embodiments, provided herein is a method of treating muscle invasive bladder cancer in an individual (such as an individual who is unfit or not eligible for a cystectomy (such as radical cystectomy)) comprising at least two or more induction phase therapies and at least one maintenance therapy, wherein each induction phase therapy comprises delivering gemcitabine continuously and locally to the bladder of the individual for about 12 week. In some embodiments, the two or more induction phase therapies are separated by a maintenance therapy. In some embodiments, provided herein is a method of treating muscle invasive bladder cancer in an individual (e.g., an individual who is unfit or not eligible for a cystectomy (such as radical cystectomy)) comprising delivering gemcitabine continuously and locally to the bladder of the individual for about 12 week (for example, the delivery comprises four consecutive delivery periods and each delivery period is about 3 weeks), wherein the individual has previously received an induction phase therapy and a maintenance therapy (such as any of the maintenance therapy described herein). In some embodiments, the induction phase therapy comprises four delivery periods (such as four consecutive delivery periods) and each delivery period is about 3 weeks (such as 18-24 days). In some embodiments, the concentration of gemcitabine in the urine of the individual is at least about 0.1 µg/mL (e.g. from about 0.1 µg/mL to about 90 µg/mL) during the delivery periods for at least about one to two weeks out of three weeks. In some embodiments, the average concentration of gemcitabine in the urine is about 5 to 20 µg/mL for at least about one to two weeks out of three weeks. In some embodiments, about 225 mg of gemcitabine is administered during each delivery period. In some embodiments, the at least one maintenance therapy comprises administering gemcitabine continuously and locally to the bladder of the individual about or at least about one, two or more times during one, two, or more delivery periods. In some embodiments, each delivery period in the maintenance phase is about or at least about one, two or three weeks. In some embodiments, there is a rest period (such as at least about 1, 2, 3, 4, 5, 6, 9, or 12 months) between two or more delivery period. In some embodiments, the delivery period in the at least one maintenance phase is about three weeks and the concentration of gemcitabine in the urine of the individual is at least about 0.1 µg/mL (e.g. from about 0.1 µg/mL to about 90 µg/mL) during the delivery periods for at least about one to two weeks out of three weeks. In some embodiments, about 225 mg of gemcitabine is administered during each delivery period during the maintenance phase.

In some embodiments, provided herein is a method of bladder preservation in an individual comprising delivering gemcitabine continuously and locally to the bladder of the individual for about 12 week. In some embodiments, the individual is at least about 70 years old (such as at least about 70, 75, 80, 85, or 90 years old). In some embodiments, the individual has a compromised immune system. In some embodiments, the individual has a cT2 or cT3 organ-confined MIBC (e.g., N0 M0 MIBC). In some embodiments, the delivery comprises four delivery periods (such as four consecutive delivery periods) and each delivery period is about 3 weeks (such as 18-24 days). In some embodiments, the concentration of gemcitabine in the urine of the individual is at least about 0.1 µg/mL (e.g. from about 0.1 µg/mL to about 90 µg/mL) during the delivery periods for at least about one to two weeks out of three weeks. In some embodiments, the average concentration of gemcitabine in the urine is about 5 to 20 µg/mL for at least about one to two weeks out of three weeks. In some embodiments, about 225 mg of gemcitabine is administered during each delivery period. In some embodiments, the method further comprises a maintenance therapy that follows the delivery of gemcitabine for about 12 weeks. In some embodiments, there is a rest period between the delivery of gemcitabine and the maintenance therapy for about 12 weeks. In some embodiments, the rest period is at least about one, two, or three months. In some embodiments, the maintenance therapy comprises administering gemcitabine continuously and locally to the bladder of the individual about or at least about one, two or more times during one, two, or more delivery periods. In some embodiments, each delivery period in the maintenance phase is about or at least about one, two or three weeks. In some embodiments, the delivery period in the maintenance phase is about three weeks and the concentration of gemcitabine in the urine of the individual is at least about 0.1 µg/mL (e.g. from about 0.1 µg/mL to about 90 µg/mL) during the delivery periods for at least about one to two weeks out of three weeks. In some embodiments, about 225 mg of gemcitabine is administered during each delivery period during the maintenance phase.

In some embodiments, provided herein is a method of alleviating a symptom of bladder cancer in an individual comprising delivering gemcitabine continuously and locally to the bladder of the individual for about 12 week. In some embodiments, alleviating a symptom comprises reducing incidences of obstruction. In some embodiments, alleviating a symptom comprises reducing frequency and or extent of hematuria or bleeding in urine. In some embodiments, alleviating a symptom comprises reducing frequency or extent of pain. In some embodiments, the symptom is alleviated for about or at least about 3 weeks, 6 weeks, 9 weeks, 12 weeks, 100 days, 120 days, 150 days, 180 days or 200 days after the initiation of the gemcitabine delivery. In some embodiments, the individual is at least about 70 years old (such as at least about 70, 75, 80, 85, or 90 years old). In some embodiments, the individual has a compromised immune system. In some embodiments, the individual has a cT2 or cT3 organ-confined MIBC (e.g., N0 M0 MIBC). In some embodiments, the delivery comprises four delivery periods (such as four consecutive delivery periods) and each delivery period is about 3 weeks (such as 18-24 days). In some embodiments, the concentration of gemcitabine in the urine of the individual is at least about 0.1 µg/mL (e.g. from about 0.1 µg/mL to about 90 µg/mL) during the delivery periods for at least about one to two weeks out of three weeks. In some embodiments, the average concentration of gemcitabine in the urine is about 5 to 20 µg/mL for at least about one to two weeks out of three weeks. In some embodiments, about 225 mg of gemcitabine is administered during each delivery period. In some embodiments, the method further comprises a maintenance therapy that follows the delivery of gemcitabine for about 12 weeks. In some embodiments, there is a rest period between the delivery of gemcitabine and the maintenance therapy for about 12 weeks. In some embodiments, the rest period is at least about one, two, or three months. In some embodiments, the maintenance therapy comprises administering gemcitabine continuously and locally to the bladder of the individual about or at least about one, two or more times during one, two, or more delivery periods. In some embodiments, each delivery period in the maintenance phase is about or at least about one, two or three weeks. In some embodiments, the delivery period in the maintenance phase is about three weeks and the concentration of gemcitabine in the urine of the individual is at least about 0.1 µg/mL (e.g. from about 0.1 µg/mL to about 90 µg/mL) during the delivery periods for at least about one to two weeks out of three weeks. In some embodiments, about 225 mg of gemcitabine is administered during each delivery period during the maintenance phase.

In some embodiments, provided herein is a method of improving life quality of an individual having bladder cancer comprising delivering gemcitabine continuously and locally to the bladder of the individual for about 12 week. In some embodiments, improving life quality comprises alleviating a symptom associated with bladder cancer, such as reducing incidences of obstruction, reducing frequency and or extent of hematuria, reducing frequency or extent of pain, and/or reducing emergency treatments. In some embodiments, the symptom is alleviated for about or at least about 3 weeks, 6 weeks, 9 weeks, 12 weeks, 100 days, 120 days, 150 days, 180 days or 200 days after the initiation of the gemcitabine delivery. In some embodiments, the individual is at least about 70 years old (such as at least about 70, 75, 80, 85, or 90 years old). In some embodiments, the individual has a compromised immune system. In some embodiments, the individual has a cT2 or cT3 organ-confined MIBC (e.g., N0 M0 MIBC). In some embodiments, the delivery comprises four delivery periods (such as four consecutive delivery periods) and each delivery period is about 3 weeks (such as 18-24 days). In some embodiments, the concentration of gemcitabine in the urine of the individual is at least about 0.1 µg/mL (e.g. from about 0.1 µg/mL to about 90 µg/mL) during the delivery periods for at least about one to two weeks out of three weeks. In some embodiments, the average concentration of gemcitabine in the urine is about 5 to 20 µg/mL for at least about one to two weeks out of three weeks. In some embodiments, about 225 mg of gemcitabine is administered during each delivery period. In some embodiments, the method further comprises a maintenance therapy that follows the delivery of gemcitabine for about 12 weeks. In some embodiments, there is a rest period between the delivery of gemcitabine and the maintenance therapy for about 12 weeks. In some embodiments, the rest period is at least about one, two, or three months. In some embodiments, the maintenance therapy comprises administering gemcitabine continuously and locally to the bladder of the individual about or at least about one, two or more times during one, two, or more delivery periods. In some embodiments, each delivery period in the maintenance phase is about or at least about one, two or three weeks. In some embodiments, the delivery period in the maintenance phase is about three weeks and the concentration of gemcitabine in the urine of the individual is at least about 0.1 µg/mL (e.g. from about 0.1 µg/mL to about 90 µg/mL) during the delivery periods for at least about one to two weeks out of three weeks. In some embodiments, about 225 mg of gemcitabine is administered during each delivery period during the maintenance phase.

In some embodiments, provided herein is a method of treating a urothelial carcinoma of the lower tract in an individual having a history of hematuria comprises delivering gemcitabine continuously and locally to the bladder of the individual for about 12 week. In some embodiments, hematuria comprises chronic hematuria, frank hematuria, occasional hematuria, and/or recurrent gross hematuria. In some embodiments, the individual has a reduced symptom of hematuria (such as a reduced frequency and/or extent of hematuria) after the delivery of gemcitabine. In some embodiments, the individual has a reduced symptom of hematuria (such as a reduced frequency and/or extent of hematuria) after the delivery of gemcitabine for at least about 3 weeks, 6 weeks, 9 weeks, 12 weeks, 120 days, 150 days, 180 days, or 200 days. In some embodiments, the individual is at least about 70 years old (such as at least about 70, 75, 80, 85, or 90 years old). In some embodiments, the individual has a compromised immune system. In some embodiments, the individual has a cT2 or cT3 organ-confined MIBC (e.g., N0 M0 MIBC). In some embodiments, the delivery comprises four delivery periods (such as four consecutive delivery periods) and each delivery period is about 3 weeks (such as 18-24 days). In some embodiments, the concentration of gemcitabine in the urine of the individual is at least about 0.1 µg/mL (e.g. from about 0.1 µg/mL to about 90 µg/mL) during the delivery periods for at least about one to two weeks out of three weeks. In some embodiments, the average concentration of gemcitabine in the urine is about 5 to 20 µg/mL for at least about one to two weeks out of three weeks. In some embodiments, about 225 mg of gemcitabine is administered during each delivery period. In some embodiments, the method further comprises a maintenance therapy that follows the delivery of gemcitabine for about 12 weeks. In some embodiments, there is a rest period between the delivery of gemcitabine and the maintenance therapy for about 12 weeks. In some embodiments, the rest period is at least about one, two, or three months. In some embodiments, the maintenance therapy comprises administering gemcitabine continuously and locally to the bladder of the individual about or at least about one, two or more times during one, two, or more delivery periods. In some embodiments, each delivery period in the maintenance phase is about or at least about one, two or three weeks. In some embodiments, the delivery period in the maintenance phase is about three weeks and the concentration of gemcitabine in the urine of the individual is at least about 0.1 µg/mL (e.g. from about 0.1 µg/mL to about 90 µg/mL) during the delivery periods for at least about one to two weeks out of three weeks. In some embodiments, about 225 mg of gemcitabine is administered during each delivery period during the maintenance phase.

In some embodiments, provided herein is a method of preventing the progression of bladder cancer in an individual comprising delivering gemcitabine continuously and locally to the bladder of the individual for about 12 week. In some embodiments, the prevention of the progression lasts about or at least about one, two, three, four, five, or six months. In some embodiments, the individual is at least about 70 years old (such as at least about 70, 75, 80, 85, or 90 years old). In some embodiments, the individual has a compromised immune system. In some embodiments, the individual has a cT2 or cT3 organ-confined MIBC (e.g., N0 M0 MIBC). In some embodiments, the delivery comprises four delivery periods (such as four consecutive delivery periods) and each delivery period is about 3 weeks (such as 18-24 days). In some embodiments, the concentration of gemcitabine in the urine of the individual is at least about 0.1 µg/mL (e.g. from about 0.1 µg/mL to about 90 µg/mL) during the delivery periods for at least about one to two weeks out of three weeks. In some embodiments, the average concentration of gemcitabine in the urine is about 5 to 20 µg/mL for at least about one to two weeks out of three weeks. In some embodiments, about 225 mg of gemcitabine is administered during each delivery period. In some embodiments, the method further comprises a maintenance therapy that follows the delivery of gemcitabine for about 12 weeks. In some embodiments, there is a rest period between the delivery of gemcitabine and the maintenance therapy for about 12 weeks. In some embodiments, the rest period is at least about one, two, or three months. In some embodiments, the maintenance therapy comprises administering gemcitabine continuously and locally to the bladder of the individual about or at least about one, two or more times during one, two, or more delivery periods. In some embodiments, each delivery period in the maintenance phase is about or at least about one, two or three weeks. In some embodiments, the delivery period in the maintenance phase is about three weeks and the concentration of gemcitabine in the urine of the individual is at least about 0.1 µg/mL (e.g. from about 0.1 µg/mL to about 90 µg/mL) during the delivery periods for at least about one to two weeks out of three weeks. In some embodiments, about 225 mg of gemcitabine is administered during each delivery period during the maintenance phase.

In some embodiments, the method of treating a urothelial carcinoma of the lower tract in an individual comprises delivering gemcitabine continuously and locally to the bladder of the individual for about 12 week. In some embodiments, the prevention of the progression lasts about or at least about one, two, three, four, five, or six months. In some embodiments, the individual is at least about 70 years old (such as at least about 70, 75, 80, 85, or 90 years old). In some embodiments, the individual has a compromised immune system. In some embodiments, the individual has a cT2 or cT3 organ-confined MIBC (e.g., N0 M0 MIBC). In some embodiments, the delivery comprises four delivery periods (such as four consecutive delivery periods) and each delivery period is about 3 weeks (such as 18-24 days). In some embodiments, the concentration of gemcitabine in the urine of the individual is at least about 0.1 µg/mL (e.g. from about 0.1 µg/mL to about 90 µg/mL) during the delivery periods for at least about one to two weeks out of three weeks. In some embodiments, the average concentration of gemcitabine in the urine is about 5 to 20 µg/mL for at least about one to two weeks out of three weeks. In some embodiments, about 225 mg of gemcitabine is administered during each delivery period. In some embodiments, the method further comprises a maintenance therapy that follows the delivery of gemcitabine for about 12 weeks. In some embodiments, there is a rest period between the delivery of gemcitabine and the maintenance therapy for about 12 weeks. In some embodiments, the rest period is at least about one, two, or three months. In some embodiments, the maintenance therapy comprises administering gemcitabine continuously and locally to the bladder of the individual about or at least about one, two or more times during one, two, or more delivery periods. In some embodiments, each delivery period in the maintenance phase is about or at least about one, two or three weeks. In some embodiments, the delivery period in the maintenance phase is about three weeks and the concentration of gemcitabine in the urine of the individual is at least about 0.1 µg/mL (e.g. from about 0.1 µg/mL to about 90 µg/mL) during the delivery periods for at least about one to two weeks out of three weeks. In some embodiments, about 225 mg of gemcitabine is administered during each delivery period during the maintenance phase.

In some embodiments, there is provided a method of maintenance therapy following at least one previous therapy for an individual having a urothelial carcinoma of the lower tract, comprising administering gemcitabine continuously and locally to the bladder of the individual one, two, or more times (e.g., two or more) during one, two or more (e.g., two or more) delivery periods, wherein each delivery period is at least one week and there is a rest period between each delivery period of at least one month. In some embodiments, the individual is at least about 70 years old (such as at least about 70, 75, 80, 85, or 90 years old). In some embodiments, the individual has a compromised immune system. In some embodiments, the individual has a cT2 or cT3 organ-confined MIBC (e.g., N0 M0 MIBC). In some embodiments, the at least one previous therapy comprises delivering gemcitabine locally and continuously to the bladder of the individual comprising four delivery periods (such as four consecutive delivery periods) and each delivery period is about 3 weeks (such as 18-24 days). In some embodiments, the concentration of gemcitabine in the urine of the individual is at least about 0.1 µg/mL (e.g. from about 0.1 µg/mL to about 90 µg/mL) during the delivery periods of the previous therapy for at least about one to two weeks out of three weeks. In some embodiments, the average concentration of gemcitabine in the urine is about 5 to 20 µg/mL for at least about one to two weeks out of three weeks. In some embodiments, about 225 mg of gemcitabine is administered during each delivery period. In some embodiments, there is a rest period between the previous therapy and the maintenance therapy for about 12 weeks. In some embodiments, the rest period is at least about one, two, or three months. In some embodiments, each delivery period in the maintenance phase is about or at least about one, two or three weeks. In some embodiments, the delivery period in the maintenance phase is about three weeks and the concentration of gemcitabine in the urine of the individual is at least about 0.1 µg/mL (e.g. from about 0.1 µg/mL to about 90 µg/mL) during the delivery periods for at least about one to two weeks out of three weeks. In some embodiments, about 225 mg of gemcitabine is administered during each delivery period during the maintenance phase.

In some embodiments, there is provided a method of treating a urothelial carcinoma of the lower tract in an individual comprising a) administering to the individual an effective amount of gemcitabine continuously and locally to the bladder of the individual during an induction phase of about 12 weeks; and b) administering to the individual an effective amount of gemcitabine continuously and locally to the bladder of the individual during a maintenance phase, wherein the induction phase and maintenance phases are separated by a rest period. In some embodiments, the rest period is at least about 1, 2, 3, 4, 5, 6, 9, or 12 months. In some embodiments, the individual is at least about 70 years old (such as at least about 70, 75, 80, 85, or 90 years old). In some embodiments, the individual has a compromised immune system. In some embodiments, the individual has a cT2 or cT3 organ-confined MIBC (e.g., N0 M0 MIBC). In some embodiments, the induction phase comprises delivering gemcitabine locally and continuously to the bladder of the individual comprising four delivery periods (such as four consecutive delivery periods) and each delivery period is about 3 weeks (such as 18-24 days). In some embodiments, the concentration of gemcitabine in the urine of the individual is at least about 0.1 µg/mL (e.g. from about 0.1 µg/mL to about 90 µg/mL) during the delivery periods of the induction phase for at least about one to two weeks out of three weeks. In some embodiments, the average concentration of gemcitabine in the urine is about 5 to 20 µg/mL for at least about one to two weeks out of three weeks. In some embodiments, about 225 mg of gemcitabine is administered during each delivery period. In some embodiments, the rest period is at least about one, two, or three months. In some embodiments, the maintenance therapy comprises administering gemcitabine continuously and locally to the bladder of the individual about or at least about one, two or more times during one, two, or more delivery periods. In some embodiments, each delivery period in the maintenance phase is about or at least about one, two or three weeks. In some embodiments, the delivery period in the maintenance phase is about three weeks and the concentration of gemcitabine in the urine of the individual is at least about 0.1 µg/mL (e.g. from about 0.1 µg/mL to about 90 µg/mL) during the delivery periods for at least about one to two weeks out of three weeks. In some embodiments, about 225 mg of gemcitabine is administered during each delivery period during the maintenance phase.

In some embodiments, there is provides a method of bladder preservation in an individual having a urothelial carcinoma of the lower tract comprising: a) administering to the individual an effective amount of gemcitabine continuously and locally to the bladder of the individual during an induction phase of about 12 weeks; and b) administering to the individual an effective amount of gemcitabine continuously and locally to the bladder of the individual during a maintenance phase, wherein the induction phase and maintenance phases are separated by a rest period. In some embodiments, the rest period is at least about 1, 2, 3, 4, 5, 6, 9, or 12 months. In some embodiments, the individual is at least about 70 years old (such as at least about 70, 75, 80, 85, or 90 years old). In some embodiments, the individual has a compromised immune system. In some embodiments, the individual has a cT2 or cT3 organ-confined MIBC (e.g., N0 M0 MIBC). In some embodiments, the induction phase comprises delivering gemcitabine locally and continuously to the bladder of the individual comprising four delivery periods (such as four consecutive delivery periods) and each delivery period is about 3 weeks (such as 18-24 days). In some embodiments, the concentration of gemcitabine in the urine of the individual is at least about 0.1 µg/mL (e.g. from about 0.1 µg/mL to about 90 µg/mL) during the delivery periods of the induction phase for at least about one to two weeks out of three weeks. In some embodiments, the average concentration of gemcitabine in the urine is about 5 to 20 µg/mL for at least about one to two weeks out of three weeks. In some embodiments, about 225 mg of gemcitabine is administered during each delivery period. In some embodiments, the rest period is at least about one, two, or three months. In some embodiments, the maintenance therapy comprises administering gemcitabine continuously and locally to the bladder of the individual about or at least about one, two or more times during one, two, or more delivery periods. In some embodiments, each delivery period in the maintenance phase is about or at least about one, two or three weeks. In some embodiments, the delivery period in the maintenance phase is about three weeks and the concentration of gemcitabine in the urine of the individual is at least about 0.1 µg/mL (e.g. from about 0.1 µg/mL to about 90 µg/mL) during the delivery periods for at least about one to two weeks out of three weeks. In some embodiments, about 225 mg of gemcitabine is administered during each delivery period during the maintenance phase.

In some embodiments, there is provided a method of treating a urothelial carcinoma of the lower tract (such as bladder cancer, for example, MIBC) in an individual comprising a) administering to the individual an effective amount of gemcitabine continuously and locally to the bladder of the individual during an induction phase comprising four consecutive delivery period, wherein each delivery period is about three weeks; and b) administering to the individual an effective amount of gemcitabine continuously and locally to the bladder of the individual during a maintenance phase comprising at least two or more delivery periods, wherein each delivery period is about three weeks, and wherein there is a rest period of at least about two months between the two or more delivery periods in the maintenance phase; and wherein the induction phase and maintenance phases are separated by a rest period of at least about three months. In some embodiments, there is provided a method of treating a urothelial carcinoma of the lower tract (such as bladder cancer, for example, MIBC) in an individual comprising a) administering to the individual an effective amount of gemcitabine continuously and locally to the bladder of the individual during an induction phase comprising four consecutive delivery period, wherein each delivery period is about three weeks; and b) administering to the individual an effective amount of gemcitabine continuously and locally to the bladder of the individual during a maintenance phase comprising two or more delivery periods, wherein each delivery period is about three weeks, and wherein there is a rest period of about two months between the two or more delivery periods in the maintenance phase; and wherein the induction phase and maintenance phases are separated by a rest period of about three months. In some embodiments, the individual is at least about 70 years old (such as at least about 70, 75, 80, 85, or 90 years old). In some embodiments, the individual has a compromised immune system. In some embodiments, the individual has a cT2 or cT3 organ-confined MIBC (e.g., N0 M0 MIBC). In some embodiments, the concentration of gemcitabine in the urine of the individual is at least about 0.1 µg/mL (e.g. from about 0.1 µg/mL to about 90 µg/mL) during the delivery periods of the induction phase and/or maintenance phase for at least about one to two weeks out of three-week delivery period. In some embodiments, the average concentration of gemcitabine in the urine is about 5 to 20 µg/mL for at least about one to two weeks out of three-week delivery period during the induction phase and/or the maintenance therapy. In some embodiments, about 225 mg of gemcitabine is administered during each delivery period during the induction phase and/or the maintenance therapy.

In some embodiments, the method of bladder preservation in an individual comprises administering to the individual an effective amount of gemcitabine, wherein the gemcitabine is delivered locally to the bladder of the individual for about 12 weeks, and wherein the individual has a cT2 bladder cancer. In some embodiments, the method of bladder preservation in an individual comprises administering to the individual an effective amount of gemcitabine, wherein the gemcitabine is delivered locally to the bladder during four delivery periods (such as four consecutive delivery periods) and each delivery period is about 3 weeks (such as 18-24 days), and wherein the individual has a cT2 bladder cancer. In some embodiments, the method of bladder preservation in an individual comprises administering to the individual an effective amount of gemcitabine, wherein the gemcitabine is delivered locally to the bladder during four delivery periods (such as four consecutive delivery periods) and each delivery period is about 3 weeks (such as 18-24 days), wherein about 225 mg of gemcitabine is administered during each delivery period, and wherein the individual has a cT2 bladder cancer. In some embodiments, the individual has an organ-confined muscle-invasive bladder cancer (such as non-metastatic MIBC (i.e., M0 MIBC), such as M0 N0 MIBC). In some embodiments, the individual has a cT2 or cT3 M0 MIBC (e.g., cT2 or cT3 N0 M0 MIBC). In some embodiments, two adjacent delivery periods is separated by a rest period. In some embodiments, the rest period is less than or no more than about 7 days, 6 days, 5 days, 4 days, 3 days, 2 days or 1 day.

In some embodiments, the method of treating a urothelial carcinoma of the lower tract in an individual comprises administering to the individual an effective amount of gemcitabine, wherein the gemcitabine is delivered locally to the bladder of the individual for about 12 weeks, and wherein the individual has a cT2 bladder cancer. In some embodiments, the method of treating a urothelial carcinoma of the lower tract in an individual comprises administering to the individual an effective amount of gemcitabine, wherein the gemcitabine is delivered locally to the bladder during four delivery periods (such as four consecutive delivery periods) and each delivery period is about 3 weeks (such as 18-24 days), and wherein the individual has a cT2 bladder cancer. In some embodiments, the method of treating a urothelial carcinoma of the lower tract in an individual comprises administering to the individual an effective amount of gemcitabine, wherein the gemcitabine is delivered locally to the bladder during four delivery periods (such as four consecutive delivery periods) and each delivery period is about 3 weeks (such as 18-24 days), wherein about 225 mg of gemcitabine is administered during each delivery period, and wherein the individual has a cT2 bladder cancer. In some embodiments, the individual has an organ-confined muscle-invasive bladder cancer (such as non-metastatic MIBC (i.e., M0 MIBC), such as M0 N0 MIBC). In some embodiments, the individual has a cT2 or cT3 M0 MIBC (e.g., cT2 or cT3 N0 M0 MIBC). In some embodiments, two adjacent delivery periods is separated by a rest period. In some embodiments, the rest period is less than or no more than about 7 days, 6 days, 5 days, 4 days, 3 days, 2 days or 1 day.

In some embodiments, the methods provided herein can be used as a method of bladder preservation in an individual. In some embodiments, the method of bladder preservation in an individual comprises administering to the individual an effective amount of gemcitabine during an induction phase and administering to the individual an effective amount of gemcitabine during a maintenance phase, wherein the gemcitabine is delivered locally to the bladder, wherein the induction phase and maintenance phases are separated by a rest period, and wherein the induction phase is about 12 weeks. In some embodiments, the individual does not receive a radical cystectomy. In some embodiments, the rest phase is about 1 month, about 2 months, about 3 months, about 4 months, about 5 months, or about 6 months. In some embodiments, the induction phase comprises administering about 900 mg gemcitabine to the individual. In some embodiments, the individual has non-muscle invasive bladder cancer. In some embodiments, the individual is ineligible for or has refused cisplatin based chemotherapy. In some embodiments, the individual has a cT2 or cT3 bladder cancer (such as cT2 or cT3 MIBC). In some embodiments, the individual has an organ-confined muscle-invasive bladder cancer (such as non-metastatic MIBC (i.e., M0 MIBC), such as M0 N0 MIBC). In some embodiments, the individual has a cT2 or cT3 M0 MIBC (e.g., cT2 or cT3 N0 M0 MIBC). In some embodiments, the induction phase comprises installing a gemcitabine releasing device every 3 weeks for a total of 12 weeks, wherein each device releases 225 mg gemcitabine. In some embodiments, the rest period is about 2-3 months, such as about 65-75 days, such as 68-27 days. The maintenance phase comprises placing a gemcitabine releasing device in the bladder of the individual comprising 225 mg gemcitabine every 3 months for 1 year. In some embodiments, the rest period is about 3 months. In some embodiments, the individual is responsive (such as having a complete response, partial response and/or stable disease) to the induction phase therapy.

In some embodiments, the method of bladder preservation in an individual comprises administering to the individual an effective amount of gemcitabine during an induction phase and administering to the individual an effective amount of gemcitabine during a maintenance phase, wherein the gemcitabine is delivered locally to the bladder, wherein the induction phase and maintenance phase are separated by a rest period, and wherein the induction phase is about 12 weeks, and wherein the individual has a cT2 bladder cancer. In some embodiments, the method of bladder preservation in an individual comprises administering to the individual an effective amount of gemcitabine during an induction phase and administering to the individual an effective amount of gemcitabine during a maintenance phase, wherein the gemcitabine is delivered locally to the bladder, wherein the induction phase comprises four delivery periods (such as four consecutive delivery periods) and each delivery period is about 3 weeks (such as 18-24 days), wherein the maintenance phase comprises administering gemcitabine to the individual about every 3 months, wherein the induction phase and maintenance phases are separated by a rest period, and wherein the individual has a cT2 bladder cancer. In some embodiments, the method of bladder preservation in an individual comprises administering to the individual an effective amount of gemcitabine during an induction phase and administering to the individual an effective amount of gemcitabine during a maintenance phase, wherein the gemcitabine is delivered locally to the bladder, wherein the induction phase comprises four delivery periods (such as four consecutive delivery periods) and each delivery period is about 3 weeks (such as 18-24 days) wherein about 225 mg of gemcitabine is administered during each delivery period, wherein the maintenance phase has a delivery period (i.e., maintenance phase delivery period) of 3 weeks every 3 months wherein about 225 mg of gemcitabine is administered during each maintenance phase delivery period, wherein the induction phase and maintenance phases are separated by a rest period, and wherein the individual has a cT2 bladder cancer. In some embodiments, the maintenance phase is about 1 year, 2 years, 3 years, 5 year, 10 years, for the lifetime of the individual, or until disease progression or toxicity. In some embodiments, the rest period is about 2-3 months, such as about 65-75 days, such as 68-72 days. In some embodiments, the rest period is about 3 months. In some embodiments, the individual is responsive (such as having a complete response, partial response and/or stable disease) to the induction phase therapy. In some embodiments, the individual has an organ-confined muscle-invasive bladder cancer (such as non-metastatic MIBC (i.e., M0 MIBC), such as M0 N0 MIBC). In some embodiments, the individual has a cT2 or cT3 M0 MIBC (e.g., cT2 or cT3 N0 M0 MIBC).

Also provided herein is a method of treating a urothelial carcinoma of the lower tract in an individual comprising administering to the individual an effective amount of gemcitabine during an induction phase and administering to the individual an effective amount of gemcitabine during a maintenance phase, wherein the gemcitabine is delivered locally to the bladder, wherein the induction phase and maintenance phases are separated by a rest period, and wherein the induction phase is about 12 weeks. In some embodiments, the method of treating a urothelial carcinoma of the lower tract in an individual comprises administering to the individual an effective amount of gemcitabine during an induction phase and administering to the individual an effective amount of gemcitabine during a maintenance phase, wherein the gemcitabine is delivered locally to the bladder, wherein the induction phase and maintenance phases are separated by a rest period, and wherein the induction phase is about 84 days. In some embodiments, the rest period is 1 month, 2 months, 3 months, 4 months, 5 months, or 6 months. In some embodiments, the individual has muscle invasive bladder cancer. In some embodiments, the individual has non-muscle invasive bladder cancer. In some embodiments, the individual is ineligible for or has refused cisplatin based chemotherapy. In some embodiments, the individual is unfit for, is ineligible, or has refused a radical cystectomy. In some embodiments, the individual has a cT2 or cT3 bladder cancer (such as cT2 or cT3 MIBC). In some embodiments, the individual has an organ-confined muscle-invasive bladder cancer (such as non-metastatic MIBC (i.e., M0 MIBC), such as M0 N0 MIBC). In some embodiments, the individual has a cT2 or cT3 M0 MIBC (e.g., cT2 or cT3 N0 M0 MIBC). In some embodiments, the rest period is about 3 months. In some embodiments, the individual is responsive (such as having a complete response, partial response and/or stable disease) to the induction phase therapy.

Also provided herein is a method of treating a urothelial carcinoma of the lower tract in an individual comprising administering to the individual an effective amount of gemcitabine during an induction phase and administering to the individual an effective amount of gemcitabine during a maintenance phase, wherein the gemcitabine is delivered locally to the bladder, wherein the induction phase and maintenance phases are separated by a rest period, wherein the induction phase is about 12 weeks, and wherein the individual has a cT2 bladder cancer. Also provided herein is a method of treating a urothelial carcinoma of the lower tract in an individual comprising administering to the individual an effective amount of gemcitabine during an induction phase and administering to the individual an effective amount of gemcitabine during a maintenance phase, wherein the gemcitabine is delivered locally to the bladder, wherein the induction phase comprises four delivery periods (such as four consecutive delivery periods) and each delivery period is about 3 weeks (such as 18-24 days), wherein the maintenance phase comprises administering gemcitabine to the individual about every 3 months, wherein the induction phase and maintenance phases are separated by a rest period, wherein the induction phase is about 12 weeks, and wherein the individual has a cT2 bladder cancer. Also provided herein is a method of treating a urothelial carcinoma of the lower tract in an individual comprising administering to the individual an effective amount of gemcitabine during an induction phase and administering to the individual an effective amount of gemcitabine during a maintenance phase, wherein the gemcitabine is delivered locally to the bladder, wherein the induction phase comprises four delivery periods (such as four consecutive delivery periods) and each delivery period is about 3 weeks (such as 18-24 days), wherein the maintenance phase comprises administering gemcitabine to the individual about every 3 months, wherein the induction phase and maintenance phases are separated by a rest period, wherein the induction phase is about 12 weeks, and wherein the individual has a cT2 bladder cancer. Also provided herein is a method of treating a urothelial carcinoma of the lower tract in an individual comprising administering to the individual an effective amount of gemcitabine during an induction phase and administering to the individual an effective amount of gemcitabine during a maintenance phase, wherein the gemcitabine is delivered locally to the bladder, wherein the induction phase comprises four delivery periods (such as four consecutive delivery periods) and each delivery period is about 3 weeks (such as 18-24 days), wherein the maintenance phase comprises administering gemcitabine to the individual about every 3 months, wherein the induction phase comprises four delivery periods (such as four consecutive delivery periods) and each delivery period is about 3 weeks (such as 18-24 days) wherein about 225 mg of gemcitabine is administered during each delivery period, wherein the maintenance phase has a delivery period (i.e., maintenance phase delivery period) of 3 weeks every 3 months wherein about 225 mg gemcitabine is administered during each maintenance phase delivery period, wherein the induction phase and maintenance phases are separated by a rest period, and wherein the individual has a cT2 bladder cancer. In some embodiments, the maintenance phase is about 1 year, 2 years, 3 years, 5 year, 10 years, for the lifetime of the individual, or until disease progression or toxicity. In some embodiments, the rest period is about 2-3 months, such as about 65-75 days, such as 68-72 days. In some embodiments, the rest period is about 3 months. In some embodiments, the individual is responsive (such as having a complete response, partial response and/or stable disease) to the induction phase therapy. In some embodiments, the individual has an organ-confined muscle-invasive bladder cancer (such as non-metastatic MIBC (i.e., M0 MIBC), such as M0 N0 MIBC). In some embodiments, the individual has a cT2 or cT3 M0 MIBC (e.g., cT2 or cT3 N0 M0 MIBC).

In some embodiments, the method of treating a urothelial carcinoma of the lower tract in an individual comprises administering to the individual an effective amount of gemcitabine during an induction phase and administering to the individual an effective amount of gemcitabine during a maintenance phase, wherein the gemcitabine is delivered locally to the bladder, wherein the induction phase and maintenance phases are separated by a rest period, wherein the induction phase is 12 weeks and the rest period is about 3 months. In some embodiments, the induction phase comprises administering about 900 mg of gemcitabine to the individual over 12 weeks. In some embodiments, the individual has muscle invasive bladder cancer. In some embodiments, the individual has non-muscle invasive bladder cancer. In some embodiments, the individual is ineligible for or has refused cisplatin based chemotherapy. In some embodiments, the individual is unfit for, is ineligible for, or has refused a radical cystectomy. In some embodiments, the individual has a cT2 or cT3 bladder cancer (such as cT2 or cT3 MIBC). In some embodiments, the individual has an organ-confined muscle-invasive bladder cancer (such as non-metastatic MIBC (i.e., M0 MIBC), such as M0 N0 MIBC). In some embodiments, the individual has a cT2 or cT3 M0 MIBC (e.g., cT2 or cT3 N0 M0 MIBC). In some embodiments, the rest period is about 3 months. In some embodiments, the individual is responsive (such as having a complete response, partial response and/or stable disease) to the induction phase therapy.

In some embodiments, the method comprises administering gemcitabine to an individual for 12 weeks, followed by a about 2-3 months rest period, followed by a maintenance phase, wherein the maintenance phase comprises administering gemcitabine to the individual about every 3 months for at least one year, wherein the gemcitabine is delivered locally to the bladder. In some embodiments, the method comprises administering gemcitabine to an individual for 12 weeks, followed by a 2-3 months rest period, followed by a maintenance phase, wherein the gemcitabine is delivered locally to the bladder, wherein the maintenance phase comprises administering about 225 mg gemcitabine to individual about every 3 months for about 1 year. In some embodiments, the maintenance phase is about 1 year, about 2 years, about 3 years, 5 year, 10 years, or for the lifetime of the individual. In some embodiments, the maintenance phase comprises delivering gemcitabine about every 3 months 2 times, 3 times, 4 times, 5 times, 6 times, or for the lifetime of the individual. In some embodiments, the maintenance phase delivery periods are each about 3 weeks (such as 18-24 days). In some embodiments, the maintenance phase delivery periods are about 1 week, about 2 weeks, or about 3 weeks. In some embodiments, the individual has muscle invasive bladder cancer. In some embodiments, the individual has non-muscle invasive bladder cancer. In some embodiments, the individual is ineligible or has refused cisplatin based chemotherapy. In some embodiments, the individual is unfit for, is ineligible, or has refused a radical cystectomy. In some embodiments, the individual has a cT2 or cT3 bladder cancer (such as cT2 or cT3 MIBC). In some embodiments, the individual has an organ-confined muscle-invasive bladder cancer (such as non-metastatic MIBC (i.e., M0 MIBC), such as M0 N0 MIBC). In some embodiments, the individual has a cT2 or cT3 M0 MIBC (e.g., cT2 or cT3 N0 M0 MIBC). In some embodiments, the rest period is about 3 months. In some embodiments, the individual is responsive (such as having a complete response, partial response and/or stable disease) to the 12-week administration of gemcitabine.

In some embodiments, provided herein is a method of treating a urothelial carcinoma of the lower tract in an individual comprising an induction phase and a maintenance phase, wherein the induction phase comprises administering about 900 mg of gemcitabine to individual over 12 weeks, wherein the maintenance phase comprises administering about 225 mg of gemcitabine to the individual about every 3 months for at least one year, wherein the gemcitabine is delivered locally to the bladder, and wherein the induction phase and the maintenance phase are separated by a rest period of about 2-3 months. In some embodiments, the individual has a cT2 or cT3 bladder cancer (such as cT2 or cT3 MIBC). In some embodiments, the individual has an organ-confined muscle-invasive bladder cancer (such as non-metastatic MIBC (i.e., M0 MIBC), such as M0 N0 MIBC). In some embodiments, the individual has a cT2 M0 MIBC. In some embodiments, the rest period is about 3 months. In some embodiments, the individual is responsive (such as having a complete response, partial response and/or stable disease) to the induction phase therapy.

In some embodiments, provided herein is a method of treating a urothelial carcinoma of the lower tract in an individual comprising an induction phase and a maintenance phase, wherein the induction phase comprises administering about 900 mg of gemcitabine to individual over 12 weeks, wherein the maintenance phase comprises administering about 225 mg of gemcitabine to the individual about every 3 months for at least one year, wherein the gemcitabine is delivered locally to the bladder, and wherein the induction phase and the maintenance phase are separated by a rest period of about 2-3 months, wherein the individual has a cT2 bladder cancer. In some embodiments, the individual has an organ-confined muscle-invasive bladder cancer (such as non-metastatic MIBC (i.e., M0 MIBC), such as M0 N0 MIBC). In some embodiments, the individual has a cT2 M0 MIBC. In some embodiments, provided herein is a method of treating a urothelial carcinoma of the lower tract in an individual comprising an induction phase and a maintenance phase, wherein the induction phase comprises administering about 900 mg of gemcitabine to individual over 12 weeks, wherein the maintenance phase comprises administering about 225 mg of gemcitabine to the individual about every 3 months for at least one year, wherein the gemcitabine is delivered locally to the bladder, and wherein the induction phase and the maintenance phase are separated by a rest period of about 2-3 months, wherein the individual has a cT3 bladder cancer. In some embodiments, the rest period is about 3 months. In some embodiments, the individual is responsive (such as having a complete response, partial response and/or stable disease) to the induction phase therapy.

In some embodiments, the induction phase comprises four delivery periods (such as four consecutive delivery periods) and each delivery period is about 3 weeks (such as 18-24 days). In some embodiments, the induction phase comprises four delivery periods (such as four consecutive delivery periods) and each delivery period is about 3 weeks (such as 18-24 days) wherein about 225 mg of gemcitabine is administered during each delivery period. In some embodiments, an intravesicular device comprising about 225 mg of gemcitabine is inserted into the bladder every 3 weeks for 12 weeks during the induction phase. In some embodiments, the individual has muscle invasive bladder cancer. In some embodiments, the individual has non-muscle invasive bladder cancer. In some embodiments, the individual is ineligible or has refused cisplatin based chemotherapy. In some embodiments, the individual is unfit for, is ineligible, or has refused a radical cystectomy. In some embodiments, the individual has a cT2 or cT3 bladder cancer (such as cT2 or cT3 MIBC). In some embodiments, the individual has an organ-confined muscle-invasive bladder cancer (such as non-metastatic MIBC (i.e., M0 MIBC), such as M0 N0 MIBC). In some embodiments, the individual has a cT2 or cT3 M0 MIBC (e.g., cT2 or cT3 N0 M0 MIBC). In some embodiments, the rest period is about 3 months. In some embodiments, the individual is responsive (such as having a complete response, partial response and/or stable disease) to the induction phase therapy.

In some embodiments, provided herein is a method of treating a urothelial carcinoma of the lower tract of an individual comprising an induction phase comprising four delivery periods (such as four consecutive delivery periods) and each delivery period is about 3 weeks (such as 18-24 days), a rest period, and a maintenance period comprising 2 or more gemcitabine delivery periods separated by about 3 months, wherein each about 225 mg of gemcitabine is administered during each delivery period. In some embodiments, the individual has a cT2 or cT3 bladder cancer (such as cT2 or cT3 MIBC). In some embodiments, the individual has an organ-confined muscle-invasive bladder cancer (such as non-metastatic MIBC (i.e., M0 MIBC), such as M0 N0 MIBC). In some embodiments, the individual has a cT2 or cT3 M0 MIBC (e.g., cT2 or cT3 N0 M0 MIBC). In some embodiments, the rest period is about 3 months. In some embodiments, the individual is responsive (such as having a complete response, partial response and/or stable disease) to the induction phase therapy.

In some embodiments, the maintenance phase is a treatment phase that follows at least one primary therapy. In some embodiments, the primary therapy is an induction therapy comprising administering gemcitabine. In some embodiments, the maintenance therapy comprises two or more gemcitabine delivery periods separated by a period of at least 1 month, wherein the delivery periods comprise administering about 225 mg of gemcitabine, wherein the gemcitabine is delivered locally to the bladder. In some embodiments, the delivery periods of the maintenance phase are separated by about 2, about 3, about 4, about 5, or about 6 months. In some embodiments, the maintenance phase comprises two or more delivery periods separated by a period of about 3 months, wherein each delivery period comprises administering about 225 mg of gemcitabine to the individual, wherein the gemcitabine is delivered locally to the bladder of the individual. In some embodiments, the maintenance phase comprises placing a gemcitabine releasing device in the bladder of the individual comprising about 225 mg gemcitabine, about every 3 months for about 1 year. In some embodiments, the maintenance phase delivery periods are each about 1 week, about 2 weeks, or about 3 weeks. In some embodiments, the maintenance phase delivery periods are each about 3 weeks (such as 18-24 days). In some embodiments, the individual has muscle invasive bladder cancer. In some embodiments, the individual has non-muscle invasive bladder cancer. In some embodiments, the individual is ineligible for or has refused cisplatin based chemotherapy. In some embodiments, the individual is unfit for, is ineligible for, or has refused a radical cystectomy. In some embodiments, the rest period is about 3 months. In some embodiments, the individual is responsive (such as having a complete response, partial response and/or stable disease) to the at least one primary therapy.

Patient Populations

The methods provided herein are useful for treatment of a range of individuals having urothelial carcinomas. For example in some embodiments, the urothelial carcinoma is a bladder cancer. In some embodiments, the bladder cancer is locally-advanced bladder cancer. In some embodiments, the bladder cancer is a metastatic bladder cancer. In some embodiments, the bladder cancer is muscle invasive bladder cancer. In some embodiments, the bladder cancer is non-muscle invasive bladder cancer. In some embodiments, bladder cancer is carcinoma in situ. In some embodiments the bladder cancer is BCG (Bacillus Calmette-Guerin) refractory cancer. In some embodiments, the bladder cancer is papillary bladder cancer. In some embodiments, the bladder cancer is grade 1/3, 2/3, or 3/3. In some embodiments, the bladder cancer is stage I, stage II, stage III, or stage IV bladder cancer. In some embodiments, the bladder cancer is high grade invasive papillary urothelial carcinoma. In some embodiments, the bladder cancer is non-invasive high grade urothelial carcinoma. In some embodiments, the bladder cancer is multifocal invasive high grade papillary urothelial carcinoma. In some embodiments the bladder cancer is cT2 or cT3. In some embodiments, the bladder is cT2 with carcinoma in situ.

In some embodiments, provided herein is a method of treating bladder cancers, (for example MIBC) in an individual who is not eligible for neoadjuvant cisplatin-based therapy comprising administering gemcitabine locally to the bladder. In some embodiments, provided herein is a method of treating bladder cancers, (for example MIBC) in an individual who refuses neoadjuvant cisplatin-based therapy comprising administering a gemcitabine locally to the bladder. In some embodiments, provided herein is a method of treating bladder cancers, (for example MIBC) in an individual having cT2 disease and an absence of high-risk features such as lymphovascular invasion (LVI), hydronephrosis, and concomitant carcinoma in situ (CIS) comprising administering a gemcitabine locally to the bladder. In some embodiments, provided herein is a method of treating bladder cancers, (for example MIBC) in an individual who will receive radical cystectomy but is ineligible for cisplatin-based neoadjuvant therapy comprising administering gemcitabine locally to the bladder. In some of these embodiments, the individual has cT2 cancer. In some embodiments, the individual has an organ-confined muscle-invasive bladder cancer (such as non-metastatic MIBC (i.e., M0 MIBC), such as M0 N0 MIBC). In some embodiments, the individual has a cT2 M0 N0 MIBC.

In some embodiments, an individual is ineligible for cisplatin-based therapy based upon co-morbidities including poor performance status, poor renal function, hearing loss, peripheral neuropathy, and cardiac disease. In some embodiments, an individual is ineligible for cisplatin-based therapy based upon the absence of one or more high-risk features such as lymphovascular invasion (LVI), hydronephrosis, and concomitant carcinoma in situ (CIS).

Accordingly, in some embodiments, provided herein is a method of treating an individual who is ineligible for cisplatin-based therapy comprising administering gemcitabine to the individual about every 3 months, wherein the gemcitabine is delivered locally to the bladder of the individual for at least 1 week. In some embodiments, about 225 mg gemcitabine is administered about every 3 months for about 1 year, about 2 years, about 4 years, or for the lifetime of the patient. In some embodiments, gemcitabine is delivered continuously for about 1 week, about 2 weeks, or about 3 weeks during the delivery periods.

In some of these embodiments, the method comprises administering about 225 mg of gemcitabine to an individual for 3 weeks about every 3 months for about 2 years. In some of these embodiments, the method comprises administering about 225 mg of gemcitabine to an individual for 3 weeks about every 3 months for about 3 years. In some of these embodiments, the method comprises administering about 225 mg of gemcitabine an individual for 3 weeks about every 3 months for the lifetime of the individual. In some embodiments the method comprises a 12 week induction phase followed by a maintenance phase.

Up until now, neoadjuvant therapy followed by radical cystectomy, or removal of the bladder has been standard therapy for treatment of muscle invasive bladder cancer. Individuals who are unfit for radical cystectomy undergo palliative transurethral resection of bladder tumors (TURBT) to attempt to limit local advancement of untreated and undertreated disease. Such treatments may temporarily manage local symptoms of hematuria, pain and urgency, but are not employed with curative intent. Therefore, in one aspect the present invention provides a method of treating bladder cancers, (for example MIBC) in an individual who is unfit or not eligible for a cystectomy by administering gemcitabine locally to the bladder.

In some embodiments, provided herein is a method of treating bladder cancers, (for example MIBC) of the lower tract in an individual who is unfit for cystectomy comprising delivering gemcitabine locally to the bladder. In some embodiments, provided herein is a method of treating bladder cancers, (for example MIBC) in an individual who is ineligible for cystectomy comprising delivering gemcitabine locally to the bladder. In some embodiments, provided herein is a method of treating bladder cancers, (for example MIBC) in an individual who is frail comprising delivering gemcitabine locally to the bladder. In some embodiments, provided herein is a method of treating bladder cancers, (for example MIBC) in an individual who cannot tolerate radical cystectomy comprising delivering gemcitabine locally to the bladder. In some embodiments, provided herein is a method of treating bladder cancers, (for example MIBC) in an individual without removing the bladder of the individual, comprising delivering gemcitabine locally to the bladder. In some embodiments, provided herein is a method of treating bladder cancers, (for example MIBC) in an individual, wherein the individual is unfit or ineligible for a cystectomy, comprising delivering gemcitabine locally to the bladder. In some embodiments, provided herein is a method of treating bladder cancer (for example MIBC) in an individual, wherein the bladder cancer is metastatic bladder cancer. In some embodiments, provided herein is a method of treating bladder cancers, (for example MIBC) in an individual, wherein the individual has cT2-cT3 disease (such as cT2-cT3 M0 disease), comprising delivering gemcitabine locally to the bladder.

In some embodiments, provided herein is a method of treating muscle invasive bladder cancer in an individual who is unfit or not eligible for a cystectomy comprising delivering gemcitabine locally to the bladder of the individual for at least 1 week every three months. In some of these embodiments, the gemcitabine may be delivered continuously to the bladder chronically, or for the lifetime of the individual to improve the quality of life of the individual. In some embodiments, about 225 mg gemcitabine is administered about every 3 months for about 1 year, about 2 years, about 4 years, or for the lifetime of the patient. In some embodiments, gemcitabine is delivered continuously for about 1 week, about 2 weeks, or about 3 weeks during the delivery periods.

In some embodiments, the individual is ineligible for or has refused cisplatin-based chemotherapy. In some embodiments, the individual is unfit for, ineligible for or has refused a radical cystectomy.

In some embodiments, the individual is ineligible for radical cystectomy under the National Comprehensive Cancer Network (NCCN) guidelines. For example, the individual may be unfit for curative therapy due to frailty. Prior to the present methods, such individuals typically received palliative radiation without chemotherapy (3.5 Gy/fraction—10 treatments; or 7 Gy/fraction—7 treatments; TURBT; or no treatment). In some embodiments the individual is unfit for platinum-based chemotherapy. In some embodiments, chemotherapy prior to radiation therapy is not recommended for the individual. In some embodiments, the individual does not receive curative therapy or systemic chemotherapy. In some embodiments, the individual has cT2-cT3 disease (such as cT2-cT3 M0 disease).

In some embodiments, the individual cannot tolerate radical cystectomy based upon the American Society of Anesthesiology (ASA) guidelines. For example the individual who cannot tolerate radical cystectomy may be deemed medically unfit for surgery requiring general or epidural anesthesia.

In other embodiments, the individual may lack operative post-operative care infrastructure or personal as determined by the Comprehensive Geriatric Assessment provided by the American Society of Anesthesiologists. Under these guidelines, an individual is deemed frail if he or she shows abnormal independent activities of daily living, severe malnutrition, cognitive impairment, or comorbidities cumulative illness rating scale for geriatrics (CISR-G) grades 3-4.

The methods of the present invention also provide important and significant treatment benefits compared to standard therapeutic regimens that call for removal of the bladder. The present invention also has the advantage of being useful as a bladder sparing protocol for individuals who are eligible for a cystectomy, but elect not to have a cystectomy. The present methods result in a greatly improved quality of life for individuals, who may be able to retain their bladder after having bladder cancer, compared to the presently available treatments. Accordingly, in some embodiments, there is provided herein is a bladder sparing method of treating bladder cancers, (for example MIBC) in an individual comprising delivering an gemcitabine locally to the bladder. In some embodiments, provided herein is a method of treating bladder cancers (for example MIBC) without removing the bladder of the individual comprising delivering gemcitabine)locally to the bladder. Also provided herein is a method of treating bladder cancers (for example MIBC), in an individual who would otherwise undergo a cystectomy comprising delivering gemcitabine locally to the bladder. In some embodiments, provided herein is a method of treating bladder cancers (for example MIBC), in an individual who is eligible for, but elects not to receive, a cystectomy, comprising delivering gemcitabine locally to the bladder. In some embodiments, provided herein is a method of bladder preservation as an alternative to radical cystectomy, comprising delivering gemcitabine locally to the bladder. In some embodiments, provided herein is a method of treating bladder cancers (for example MIBC), in an individual who elects not to undergo a cystectomy, comprising delivering gemcitabine locally to the bladder. In some embodiments, provided herein is a method of preserving the bladder of an individual, comprising delivering gemcitabine locally to the bladder. In some embodiments, provided herein is a method of treating bladder cancers (for example MIBC), in an individual, without removing the bladder, comprising delivering an an gemcitabine locally to the bladder. In some embodiments, provided herein is a method of treating a CT2 urothelial carcinoma in an individual who would otherwise receive a cystectomy, comprising delivering gemcitabine locally to the bladder of the individual.

In some embodiments, the present methods are especially suited for treatment of individual with CT2 patients who would typically receive a radical resection followed by neoadjuvant therapy. The present methods result in local/ regional (locoregional) control of the disease, including nodes, and thus can be used for long-term treatment in this bladder sparing population. The present methods also result in freedom from invasive recurrence, good long term bladder function, and low rates of salvage cystectomy, all of which are of major importance in the elderly, relatively frail population of individuals with bladder cancer who have an average age of 70.

In some embodiments, the present methods are applicable to subjects that have a history of hematuria (such as chronic hematuria, frank hematuria, recurrent gross hematuria, or recurrent hematuria). The present methods reduce and/or control the symptom of hematuria, for as long as about 200 days.

In some embodiments, the individual has muscle-invasive bladder cancer (MIBC). In some embodiments, the individual has non-muscle invasive bladder cancer (NMIBC).

In some embodiments, the individual has non-metastatic (M0) bladder cancer (e.g., MIBC). In some embodiments, the individual has N0 bladder cancer (e.g., MIBC). In some embodiments, the individual has N1, N2, or N3 bladder cancer (e.g., MIBC). In some embodiments, the individual has cT2 bladder tumor or cT3 bladder tumor (e.g., MIBC). In some embodiments, the individual has Ta, Tis, T1, T2 (e.g., T2a and/or T2b), T3 (e.g., T3a and/or T3b), T4 (e.g., T4a and/or T4b) bladder cancer (e.g., MIBC). In some embodiments, the individual has N0 and M0 bladder cancer (e.g., MIBC). In some embodiments, the individual has cT2, N0, M0 MIBC. In some embodiments, the individual has cT3, N0, M0 MIBC.

In some embodiments, the individual is at least about 60, 65, 70, 75, 80, 85 or 90 years old. In some embodiments, the individual has a compromised immune system.

In some embodiments, the individual is human.

II. Intravesicular (intravesical) Devices

Device Shape

In some embodiments, the methods provided herein comprise administering gemcitabine using an intravesicular (intravesical) device. In some embodiments, the intravesicular (intravesical) device comprises a deployment shape and a retention shape. For example, the device may be elastically deformable between a relatively straightened or uncoiled shape suited for insertion through a lumen (e.g., the urethra) into the bladder of the individual (the deployment shape) and a retention shape suited to retain the device within the bladder. For the purposes of this disclosure, terms such as "relatively expanded shape," "relatively higher-profile shape," or "retention shape" generally denote any shape suited for retaining the device in the intended implantation location, including but not limited to a pretzel shape or other coiled shape (e.g., comprising bi-oval or overlapping coils) that is suited for retaining the device in the bladder. The retention shape provides that the device resists becoming entrained in urine and excreted when the individual voids. Similarly, terms such as "relatively lower-profile shape" or "deployment shape" generally denote any shape suited for deploying the drug delivery device into the body, for example the bladder, including, but not limited to, including a linear or elongated shape that is suited for deploying the device through the working channel of catheter, cystoscope, or other deployment instrument positioned in the urethra. In embodiments, the drug delivery device may naturally assume the relatively expanded shape and may be deformed, either manually or with the aid of an external apparatus, into the relatively lower-profile shape for insertion into the body.

For example, the external apparatus may be an inserter configured for transurethral insertion. Once deployed the intravesicular (intravesical) device may spontaneously or naturally return to the initial, relatively expanded shape for retention in the body. In some embodiments, the device behaves like a spring, deforming in response to a compressive load (e.g., deforming the device into a deployment shape) but spontaneously returning to a retention shape once the load is removed.

In some embodiments, the shape changing functionality of the intravesicular (intravesical) device described in the preceding paragraph may be provided by including a shape retention frame (i.e., a "retention frame") in the device, such as those disclosed in the patent applications publications identified above and incorporated herein by reference. In some embodiments, the device may include a retention frame lumen in which the retention frame, which may be an elastic wire, e.g., a superelastic alloy such as nitinol, is secured. The retention frame may be configured to return spontaneously to a retention shape, such as a "pretzel" shape or another coiled shape, such as those disclosed in the applications previously incorporated. In particular, the retention frame may retain the device in the body, such as in the bladder. The retention shape provides that the device resists becoming entrained in urine and excreted when the individual voids. For example, the retention frame may have an elastic limit and modulus that allows the device to be introduced into the body in a relatively lower-profile shape, permits the device to return to the relatively expanded shape once inside the body, and impedes the device from assuming the relatively lower-profile shape within the body in response to expected forces, such as the hydrodynamic forces associated with contraction of the detrusor muscle and urination. Thus, the device may be retained in the individual's bladder once deployed, limiting or prevent accidental expulsion.

In some other embodiments, the shape changing functionality of the intravesicular (intravesical) device may be provided by forming the device housing at least in part of a thermally shape set elastic polymer.

The material used to form the device body (i.e., the housing), at least in part, may be elastic or flexible to permit moving the device between deployment and retention shapes. When the device is in the retention shape, the retention frame portion may tend to lie inside the drug reservoir portion as shown, although the retention frame portion can be positioned inside, outside, above, or below the drug reservoir portion in other cases. The material used to form the device body may be water permeable so that solubilizing fluid (e.g., urine) can enter the drug reservoir portion to solubilize the non-liquid forms of the gemcitabine, immunomodulating agent, additional therapeutic agent, functional agent, or combination thereof contained in the drug reservoir once the device is deployed into the bladder. For example, silicone or another biocompatible elastomeric material may be used. In other embodiments, the device body may be formed, at least in part, of a water-impermeable material.

In some embodiments, the device body is made of an elastic, biocompatible polymeric material. The material may be non-resorbable or resorbable. Example non-resorbable materials include synthetic polymers selected from poly (ethers), poly(acrylates), poly(methacrylates), poly(vinyl pyrolidones), poly(vinyl acetates), poly(urethanes), celluloses, cellulose acetates, poly(siloxanes), poly(ethylene), poly (tetrafluoroethylene) and other fluorinated polymers, and poly(siloxanes). Example resorbable materials, specifically biodegradable or bioerodible polymers, include synthetic polymers selected from poly(amides), poly(esters), poly (ester amides), poly(anhydrides), poly(orthoesters), polyphosphazenes, pseudo poly(amino acids), poly(glycerol-sebacate), poly(lactic acids), poly(glycolic acids), poly(lactic-co-glycolic acids), poly(caprolactones), poly(caprolactone) (PC) derivatives, amino alcohol-based poly(ester amides) (PEA) and poly (octane-diol citrate) (POC), and other curable bioresorbable elastomers. PC-based polymers may require additional cross-linking agents such as lysine diisocyanate or 2,2-bis(e-caprolacton-4-yl)propane to obtain elastomeric properties. Copolymers, mixtures, and combinations of the above materials also may be employed.

In some embodiments, the device body comprises silicone, thermoplastic polyurethane, ethyl vinyl acetate (EVA), or a combination thereof. In some embodiments, the device body comprises two different thermoplastic materials, one of which is a hydrophilic thermoplastic polyurethane and is drug permeable, with the other being drug-impermeable. The drug impermeable material may be a selected from the group consisting of hydrophilic polyurethane, hydrophilic polyesters, and hydrophilic polyamides. The device body may comprise an annular tube formed by an extrusion or coextrusion process, using one or more these materials, as described in U.S. Publication 2016/0310715.

Drug Core

In embodiments in which the anti-metabolite is delivered from an intravesical (intravesicular) drug delivery device, the drug may be housed in the device in various forms, which may depend on the particular mechanism by which the device controllably releases the drug into fluid (e.g., urine) in the bladder. In some embodiments, the drug is provided in a solid, semi-solid, or other non-liquid form, which advantageously may facilitate stable storage of the drug before the device is used and advantageously may enable the drug payload of the device to be stored in smaller volume than would be possible if the drug were housed in the form of a liquid solution. In an embodiment, the non-liquid form is selected from tablets, granules, powders, semisolids (e.g., an ointment, cream, paste, or gel), capsules, and combinations thereof. In one embodiment, the drug is in the form of a plurality of tablets, such as mini-tablets described in U.S. Pat. No. 8,343,516.

For example, the anti-metabolite, may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

In one embodiment, the gemcitabine is formulated with one or more excipients that include a viscosity enhancing agent to control release of solubilized gemcitabine from a release aperture in the device housing. In another embodiment, the device reservoir includes both gemcitabine and a viscosity enhancing agent, but they are not co-formulated and instead are provide in discrete regions within the reservoir, e.g., as separate tablets. Suitable viscosity enhancing agents, including but not limited to polyethylene oxide (PEO), are known in the pharmaceutical arts. In some variations of the embodiment, the viscosity enhancing agent may be provided, e.g., formulated, with urea or another osmotic agent.

In one embodiment, the gemcitabine is administered to the individual with a solubility enhancing agent. In an embodiment, the solubility enhancing agent is urea. In one embodiment, the urea is provided in a tablet or other solid form and loaded with the gemcitabine in the drug reservoir of an intravesicular (intravesical) drug delivery device. The urea may also function, depending on the device, as an osmotic agent to facilitate generation of an osmotic pressure in a drug reservoir. In a particular embodiment, the gemcitabine and the osmotic agent are configured as separate tablets (or other solid forms) positioned within different regions of the drug reservoir as described in PCT WO 2015/026813 (Lee et al.) which is incorporated by reference herein.

In some embodiments the device may comprise a drug reservoir lumen. In some of these embodiments, each drug reservoir lumen may hold one or several drug tablets or other solid drug units. In one embodiment, the device holds from about 10 to 100 cylindrical drug tablets, such as mini-tablets, among a number of discrete drug reservoir lumens. In certain embodiments, the mini-tablets may each have a diameter of about 1.0 to about 3.3 mm, such as about 1.5 to about 3.1 mm, and a length of about 1.5 to about 4.7 mm, such as about 2.0 to about 4.5 mm.

Drug Housing

The release of gemcitabine from the intravesicular (intravesical) devices described herein may be driven and controlled by different mechanisms of action. In various embodiments, the drug may be released from the intravesicular (intravesical) drug delivery device by diffusion through a wall of the drug housing, by diffusion through one or more defined apertures in a wall of the drug housing, by osmotic pressure through an aperture in the drug housing, by osmotic pressure through one or more transiently formed microchannels, by erosion of a drug formulation in contact with urine in the bladder, or by a combination thereof. In some embodiments, drug release is controlled by drug diffusion through a drug-permeable polymer or matrix component defining part of the device housing. In one embodiment, the device includes a drug-permeable polymer component.

The size of the housing, including the thickness of the wall, may be selected based on the volume of drug (and functional agent, if any) formulation(s) to be contained, the desired rate of delivery of the drug from the device body/housing, the intended site of implantation of the device within the body, the desired mechanical integrity for the device, the desired release rate or permeability to water and urine, the desired induction time before onset of initial release, and the desired method or route of insertion into the body, among others. In embodiments in which the housing is a tube, the tube wall thickness may be determined based on the mechanical properties and water permeability of the tube material, as a tube wall that is too thin may not have sufficient mechanical integrity while a tube wall that is too thick may experience an undesirably long induction time for initial drug release from the device and/or may not have sufficient flexibility to permit delivery through a urethra or other narrow body lumen.

In some embodiments, the housing may be an elongated, annular tube having an inner diameter from about 2 mm to about 5 mm. The drug, and functional agent if any, may be solid tablets having a diameter substantially the same as the inner diameter of the elongated annular tube. In some embodiments, the housing holds one or more first drug units comprising a drug and one or more second drug units comprising a functional agent which facilitates release of the drug. One or more of the first unit tablets may fill a length from about 1 cm to about 3 cm of the lumen of the tube, and one or more of the second unit tablets may fill a length from about 10 cm to about 15 cm of the lumen of the tube. In one embodiment, the ratio of volume of the first unit(s) to volume of the second unit(s) is from about 0.05 to about 0.5. Other lengths and ratios of the tablet payloads are envisioned.

In some embodiments, the housing may be an elongated, annular tube having a wall thickness from 0.1 to 0.4 mm, such as a wall thickness of 0.2 mm. The housing material may comprise one or more biocompatible elastomers. The housing material may be selected such that the housing has a durometer from 25A to 80A, such as 25A, 50A, 65A, 70A, or 80A.

In various embodiments, the intravesicular (intravesical) device may release the drug continuously or intermittently to achieve a concentration of the drug in the bladder that produces a sustained, therapeutically effective concentration of the drug in urine in the bladder as described in the methods provided herein. For example, over a period from 1 hour to 1 month, for example from 2 hours to 2 weeks, from 6 hours to 1 week, from 24 hours to 72 hours, etc. In certain embodiments, the intravesicular (intravesical) device may release the gemcitabine in an amount of from 1 mg/day to 1000 mg/day, for example from 20 mg/day to 300 mg/day or from 25 mg/day to 300 mg/day. In certain embodiments, these release rates are provided over a treatment period as described herein. In certain embodiments, these release rates are provided over a treatment period from 14 days to 21 days.

Osmotic and Diffusion Systems

Following in vivo deployment, the device releases the drug. Release may occur, as described above, due to an osmotic pressure gradient between the interior and exterior of the device, the drug passing through one or more orifices or passing pores in the device under the force of osmotic pressure. Release may also occur by diffusion, whereby the drug passes through one or more orifices or passing pores in the device and/or through a drug-permeable wall of the device, due to a drug concentration gradient between the interior and exterior of the device. Combinations of these release modes within a single device are possible, and in some embodiments are preferred in order to achieve an overall drug release profile not readily achievable from either mode individual.

In some embodiments in which the device comprises a drug in a solid form, elution of drug from the device occurs following dissolution of the drug within the device. Bodily fluid enters the device, contacts the drug and solubilizes the drug, and thereafter the dissolved drug diffuses from the device or flows from the device under osmotic pressure or via diffusion. For example, the drug may be solubilized upon contact with urine in cases in which the device is deployed in the bladder. In certain embodiments, a water permeable wall portion of the housing is permeable to the drug in aqueous solution, such that solubilized drug is released via the wall portion, also referred to herein as "trans-wall diffusion." After the device is implanted, water or urine permeates through the wall, enters the reservoir, and solubilizes the functional agent and/or drug. The drug then diffuses directly through the wall at a controlled rate, due to a drug concentration gradient between the interior and the exterior of the device. For example, the housing and/or any water or drug permeable wall portions may be silicone, a thermoplastic polyurethane, ethylene-co-vinyl acetate (EVA), or a combination thereof.

In some embodiments, the intravesicular (intravesical) device may contain a unit concentration of about 225 mg of gemcitabine. In some of these embodiments, the device may be configured to deliver about 100 to about 225 mg of gemcitabine (e.g., about 140 mg, about 160 mg, about 180 mg, about 200 mg, or about 220 mg) mg of gemcitabine to the individual over a 3 week period.

In a particular embodiment, the drug delivery device may include a permeation system as described in WO2014/145638 and U.S. Publication 2016/0310715, which are herein both incorporated by reference in its entirety. In some embodiments, the drug delivery device includes a housing having a closed drug reservoir lumen bounded by a first wall structure and a hydrophilic second wall structure; and a drug formulation comprising gemcitabine contained in the drug reservoir lumen, wherein the first wall structure is permeable or impermeable to water and impermeable to the drug, and the second wall structure is permeable to the gemcitabine.

In some embodiments, the device housing has walls bounding and defining the drug reservoir of the device that are made of a first material that serves as the first wall structure and a second material that serves as the second wall structure, such that drug release occurs essentially only through the second material. In one embodiment, the device does not include an aperture; drug release is only by diffusion through the second wall structure. As used herein, the terms "impermeable to the drug" and "impermeable to water" refer to the wall structure being substantially impermeable to the drug or to water, such that essentially no drug or water is released via the wall structure over the therapeutic release period. For use in the bladder, it is desirable that the device be compliant (i.e., easily flexed, soft feeling) during detrusor muscle contraction in order to avoid or mitigate discomfort and irritation to the patient. Thus, the durometer of the first and second materials of construction are a design consideration, and the proportion of a high durometer material may be limited in constructing a device housing of a given size while keeping it suitably compliant in the bladder. For example, Tecophilic™ thermoplastic polyurethane (Lubrizol Corp.) may have a Shore hardness greater than 70A, such as from 80A to 65D, while silicone tubing which may have a Shore hardness of from 50A to 70A. Accordingly, it can be advantageous to utilize the combination of these two different polymeric materials, rather than making the device entirely of the water-swelling hydrophilic, drug-permeable second material.

The arrangement of the first and second wall structures can take a variety of forms. In certain embodiments, the first wall structure is a cylindrical tube and the second wall structure is an end wall disposed at least one end of the cylindrical tube, or the first wall structure and the second wall structure are adjacent one another and together form a cylindrical tube. That is, drug release is controlled by drug diffusion through a drug-permeable component defining a portion of the closed device housing. The drug-permeable wall structure may be located, dimensioned, and have material properties to provide the desired rate of controlled drug diffusion from the device. In one embodiment, the drug permeable wall may include a disk stabilized in the lumen of a tube at or near an end of the tube, optionally sandwiched between an inner washer and an outer washer. In another embodiment, the drug permeable wall is part of a sidewall of a tubular housing, or part of an end plug located at the end of a tubular housing.

The length and width, e.g., wall portion formed of the water permeable material are selected to provide a desired rate of water flux into the reservoir defined by device housing. In one embodiment, the width of the water permeable wall portion may be quantified by the arc angle defining the wall when viewed in cross-section normal to the luminal axis. The water permeable region(s) of the device housing can be controlled to give a selected area of, and thus rate for, osmotic water imbibition, and yet advantageously maintain suitable overall dimensions and elasticity of the device, formed of suitable biocompatible elastomers. Advantageously by forming the device housing by a co-extrusion process, the structural variations of the water permeable region(s) can be created with conventional co-extrusion equipment by selection of the processing parameters, thereby beneficially providing the ability to cost-effectively manufacture multiple structural device configurations. In some embodiments, the length of the water permeable regions(s) runs along only a portion of the overall length of the device. In such an embodiment, larger arc angles of the water permeable region(s) can therefore be employed while keeping the rate of drug release at a desirable level over an extend period of time.

In some embodiments, the wall may have a varied thickness over the circumference of the wall, for example the drug permeable portion may have a thickness that is less than the thickness of the drug impermeable portion. Moreover, the thinner drug permeable wall structure may be disposed at various positions relative the adjacent, thicker drug impermeable wall structure. In some embodiments, drug release is controlled by drug diffusion through a drug-permeable component defining a portion of the closed device housing. The drug-permeable wall structure may be located, dimensioned, and have material properties to provide the desired rate of controlled drug diffusion from the device.

In some embodiments, the drug delivery device comprises a housing comprising a first wall structure and a second wall structure that are adjacent one another and together form a tube defining a drug reservoir lumen; and a drug contained in the drug reservoir lumen, wherein: (i) the second wall structure, or both the first wall structure and the second wall structure, are permeable to water, (ii) the first wall structure is impermeable to the drug and the second wall structure is permeable to the drug, such that the drug is releasable in vivo by diffusion through the second wall structure, (iii) the second wall structure comprises less than 90 percent of a cross sectional area of the tube, in a cross section normal to the longitudinal axis of the tube, (i v) and the first wall structure comprises a first polyurethane composition.

In some embodiments, the device comprises an elongated, elastic housing having a drug reservoir lumen extending between a first closed end and a second closed end; and a drug contained in the drug reservoir lumen, wherein (i) the housing comprises a tubular wall structure which comprises: a first annular segment formed entirely of a first material which is impermeable to the drug, and a second annular segment formed at least partially of a second material which is permeable to the drug and configured to release the drug in vivo by diffusion through the second material in the second annular segment, and (ii) the first annular segment has a first end which is integrally formed and connected with a first end of the second annular segment.

In some embodiments, the walls that define the drug reservoir lumens may have varying thickness. Housings with walls of different thicknesses may improve the housing's flexibility, compressibility, or both. Different wall thicknesses also may aid in securing a solid drug unit in the drug reservoir lumens.

In some embodiments, the intravesicular (intravesical) device body, or housing, may include openings (e.g., at the opposed ends of an annular tube) in need of sealing following loading of the drug reservoir with the drug payload, during the assembly process. Any of these defined openings or ends of the housings, including the monolithic housing and modular housing units, may be sealed, if desired to close off an opening. This sealing may be accomplished with a sealing substance or structure. The sealing structure may be formed of biocompatible material, including a metal such as stainless steel, a polymer such as silicone, a ceramic, or sapphire, or adhesive, among others or combinations thereof. The sealing substance or structure may be biodegradable or bioerodible. In one embodiment, a medical grade silicone adhesive or other adhesive is loaded into the opening in a fluid or workable form and then cure within the housing opening to seal it. In some embodiments, the housing includes one or more predefined apertures for release of the drug from the device. These drug-release apertures are not the defined openings which are sealed. In other embodiments, the housing does not include a predefined drug-release aperture.

In some embodiments the device releases drug without a predefined drug release aperture (i.e., orifice). Release of drug from a device without a predefined drug-release aperture may be driven by diffusion or osmotic pressure. Examples of such suitable "no-orifice" release systems are described in PCT Patent Application Publication No. WO 2014/144066 (TB 130) and U.S. Patent Application Publication No. 2014/0276636 (TB 134), which are incorporated herein by reference.

In a particular embodiment, the drug delivery device may include an osmotic system as described in U.S. Publication 2016/0199544, U.S. Pat. No. 8,679,094, and U.S. Publication 2016/0008271, which are herein incorporated by reference.

In some embodiments, the device comprises a housing defining a reservoir; a first unit contained within the reservoir, the first unit comprising a drug; and a second unit contained within the reservoir in a position distinct from the first unit, wherein the second unit comprises a functional agent that facilitates in vivo release of the drug from housing. In some embodiments, the first unit comprises one or more solid tablets which comprise at least one drug (such as gemcitabine), and the second unit comprises one or more solid tablets (e.g., which comprise an osmotic agent, such as urea). In some embodiments, the housing is in the form of an elongated elastomeric tube having a lumen (i.e., the reservoir) in which all of the solid tablets of the first and second units are aligned and contained. The diameter of the solid tablets may be substantially the same as the diameter of the lumen.

When osmotic release is the desired drug release mode, the functional agent in the second units may include an osmotic agent that facilitates osmotic release of the drug. For example, the osmotic agent may have a higher solubility than the drug, such that the osmotic agent expedites solubilization and/or subsequent release of the drug. This beneficially allows for the delivery of low solubility or other drugs typically only delivered via diffusion, from osmotic delivery-based devices. The device may exhibit an induction period while a sufficient volume of functional agent and/or drug are solubilized to achieve the osmotic pressure gradient.

Subsequently, the device may exhibit a zero-order release rate for an extended period, followed by a reduced, non-zero-order release rate over a decay period. A desired delivery rate can be achieved by controlling/selecting various parameters of the device, including but not limited to the surface area and thickness of the water permeable wall; the permeability to water of the material used to form the wall;

the shape, size, number and placement of the apertures; and the dissolution profiles of the drug and functional agent.

The devices described herein may also be configured to release drug via diffusion, alone or in combination with osmotic release. The device may be configured to allow the solubilized drug to pass through a portion of the housing or one or more apertures therein.

Alternatively, or in combination with a water permeable wall portion, the housing may include at least one aperture configured to permit a fluid to enter the reservoir in vivo. The housing may also include one or more apertures or passing pores configured to permit solubilized drug to pass there through.

In some embodiments of the osmotic system, the device housing includes a first elastomeric material that is water permeable and a second elastomeric material that is water impermeable, wherein both materials are selected to be impermeable to the drug contained in the housing.

Erosion-Based Systems

In some embodiments, which may be used with tablets comprising low-solubility drugs, the drug is provided in tablet form secured in the device with exposed tablet faces, such that release of drug from the device occurs by controlled erosion/dissolution, as described in U.S. Pat. No. 9,107,816. In some embodiments, the device may comprise modular housings. The modular housings are typically formed from at least two separate housing units, each unit housing at least one solid drug unit. The material from which each housing unit is formed defines at least one drug reservoir lumen capable of housing a solid drug unit. The drug reservoir lumens may have one or more defined openings. For example, the drug reservoir lumen may have two opposed openings which expose correspondingly opposed end surfaces of the at least one solid drug unit housed therein. In certain embodiments, the at least two separate housing units in the modular housings are connected, directly or indirectly, by a retention frame. In some embodiments, the modular housing units may be placed on the retention frame to form a "bracelet" design. The devices may have one housing unit or a plurality of housing units. The number of housing units may be limited only by the size of the retention frame by which they are connected.

In some embodiments, one or more of the separate housing units includes a retention frame lumen through which a shared retention frame is extended. In certain embodiments, the retention frame lumen and the drug reservoir lumen of each housing unit are arranged parallel to each other. In particular embodiments, the retention frame lumen and the drug reservoir lumen of each housing unit are arranged perpendicular to each other. In further embodiments, the retention frame lumen and the drug reservoir lumen of each housing unit are arranged at an angle other than 0° (parallel) and 90° (perpendicular), such as 5, 10, 30, 45, 60, or 85°. In further embodiments, the devices described herein include two or more housing units with at least two of the following configurations: (1) the retention frame lumen and drug reservoir lumen are arranged substantially parallel to each other, (2) the retention frame lumen and drug reservoir lumen are arranged substantially perpendicular to each other, and (3) the retention frame lumen and drug reservoir lumen are arranged at an angle other than 0° (parallel) and 90° (perpendicular).

Integrated Silicone Drug Delivery Systems

In some embodiments, the device may comprise an elastic polymer-drug matrix as described in WO2015/200752, which is herein incorporated by reference in its entirety.

Devices with Multiple Release Portions

In particular embodiments, the device includes at least two drug release portions, at least one release portion releasing drug at a different rate than another release portion as described in WO2011/031855 which is herein incorporated by reference in its entirety. The release portions may achieve different release rates by having different configurations, by housing different drug formulations, or by employing different release mechanisms, among others or combinations thereof. The release portions may be combined to achieve a desired release profile. For example, the device may include release portions that exhibit different induction or lag times before the onset of initial release, that release drug at different rates or according to different release curves after the onset of release, or that release drug for different periods before the drug load is substantially exhausted, among others or combinations thereof. The disparate release portions may be combined to achieve a desired release profile from the drug delivery device as a whole, such as a release profile that demonstrates a relatively short initial lag time and thereafter demonstrates continued release at a relatively constant rate over an extended period.

In some embodiments, the devices are loaded with drugs in the form of a number of solid drug tablets, which may be smaller in size than conventional drug tablets. Because the devices control release of the drug into the body, the drug itself may include little or no excipients that control drug release. Instead, the excipients present in the drug tablets may be present primarily or completely to facilitate the tableting process or solubilization in vivo. Thus, the devices may provide a high drug payload on a volume or weight basis, yet the devices may be small enough for in vivo deployment in a minimally invasive manner.

The drug housing also permits the egress of drug, in either liquid or semi-solid form as implanted or following in vivo solubilization. The wall may be formed from a drug-permeable material that permits drug efflux through the drug housing along its entire length. The wall also may be formed from a material that is semi-permeable to the drug depending at least in part on the drug form. For example, the wall may be permeable to the drug in one form, such as a charged form, but not another form, such as uncharged form (e.g., base form versus salt form). The wall also may include one or more openings or passageways formed completely through it that permit drug to exit the drug housing.

The drug housing houses a drug in the form of a number of solid drug tablets, which are aligned within the drug housing in a serial arrangement and are enclosed within the drug housing with sealing structures, such as plugs, that close entry openings on opposite ends of the drug housing. Interstices or breaks formed between adjacent drug tablets permit the drug tablets to move with reference to each other so that the device is flexible despite being loaded with drug in solid form.

The drug portion can have any combination of the characteristics or configurations described herein, meaning the aperture may be provided, omitted, substituted with a passing pore, or augmented with additional apertures or passing pores; the housing may have a porous wall with an open-cell structure or a closed-cell structure; one or more degradable timing structures or release modulating structures may be associated with the housing, or any combination thereof.

The drug tablets may be aligned in any arrangement other than a serial arrangement, depending on the configuration of the drug housing. The drug tablets may fill any portion of the drug housing other than the entire drug housing as illustrated. A filling material such as silicone adhesive can be used to fill any portion of the drug housing that is not loaded with drug tablets, or air may be used, increasing the buoyancy of the device. The composition of the drug tablets may be the same or may vary along the device. The drug also may be in forms other than a drug tablet, such as other liquid, semi-solid, or solid forms (e.g., granules).

In particular embodiments, the drug delivery device includes at least two discrete or segregated drug portions associated with a single retention portion. The drug portions may be separate drug housings each associated with the retention portion, or the drug portions may be separate areas within a single drug housing that is associated with the retention portion.

Each drug portion may be defined by a portion of the wall of the drug housing and at least one partition structure, which separates the drug portion from a second drug portion. The partition structure may be a plug inserted into the housing, such as a cylinder, sphere, or disk, among others, which is secured in place due to its size or with an adhesive. The partition structure also may be a portion of the housing formed directly therein, such as by molding.

A device with at least two discrete portions may be suited for controlled release of at least two drug payloads from a corresponding number of drug reservoirs. The two discrete portions may have the same configurations or different configurations as described herein. The two drug payloads may be the same as each other or may differ from each other with reference to content, such as active ingredient content or excipient content; form, such as salt form or base form; state, such as liquid, semi-solid, or solid state; among others or combinations thereof. Thus, the two discrete portions may release the two drug payloads at the same time or at different times, at the same rate or at different rates, via the same release mechanisms or different release mechanisms, or any combination thereof.

For example, one drug portion may be configured to release its drug payload relatively quickly after implantation and another drug portion may be configured to experience an induction time before beginning release, or a combination thereof. The onset of release of two payloads in different drug portions can be staged. Examples of quick release drug portions include a drug portion that operates as a relatively fast-acting osmotic pump, such as a silicone tube having a relatively thinner wall, a drug portion that is loaded with drug in a quick release form, such as liquid form or a specially formulated solid form, a drug portion associated with a relatively fast-acting degradable timing structure, or combinations thereof. Thus, the device may release drug during an initial, acute phase and during a maintenance phase.

As another example, one drug portion may be configured to release its drug payload at a relatively faster rate than the other drug payload. For example, one drug portion may house a drug payload with low water solubility for diffusive release that is initiated relatively soon after implantation, and another drug portion may house a drug payload that is highly water soluble for osmotic release after an induction period. As another example, one drug portion may house a drug payload in a liquid state for quick release through an aperture having a fast-acting degradable timing membrane, and another drug portion may house another drug payload of solid tablets for slow release following solubilization in vivo. As still another example, one drug portion may have a relatively solid wall while another drug portion may have a number of apertures or pores formed through its wall, which may increase the release rate due to diffusion, or a closed-cell porous wall, which may increase the release rate due to increased permeation of water or drug through the wall.

The release portions may be combined to achieve a desired release profile. For example, the device may include release portions that exhibit different induction or lag times before the onset of initial release, that release drug at different rates or according to different release curves after the onset of release, or that release drug for different periods before the drug load is substantially exhausted, among others or combinations thereof. The disparate release portions may be combined to achieve a desired release profile from the drug delivery device as a whole, such as a release profile that demonstrates a relatively short initial lag time and thereafter demonstrates continued release at a relatively constant rate over an extended period.

By combining multiple distinct drug portions in a single device, the device may exhibit a desired release profile of an anti-metabolite. The release profile from the device as a whole may be the sum of the release profiles of the discrete portions, for example, with the first portion exhibiting minimal lag time before the onset of release, the second portion exhibiting a short induction period as the osmotic pressure gradient develops, and the third portion exhibiting a longer delay before onset as the degradable structure dissolves or degrades. Once release begins from any one portion, the release rate may be relatively zero-order for an extended period, followed by a period of decay. It should be noted that the three discrete portions are examples, and that any number or combination of discrete portions may be used to achieve the desired release profile.

Because the different drug portions are merely segregated areas within in a single tubular housing, the device advantageously may be relatively simple to construct and deploy, and yet the different drug portions exhibit different release profiles due to the different drug payloads, aperture placement, and degradable timing structures. In other embodiments in which the drug portions use, for example, walls of different materials, thicknesses, or porous cell structures, the housing may vary along its length or separate drug housings may be used. Thus, controlled release may be achieved in a range of manners.

Gels

In another embodiment, a coating substance may be intravesically applied to the bladder wall (e.g., to an area of the urothelium inside the urinary bladder), wherein the coating substance includes the gemcitabine or other drug and one or more excipient materials that promote adherence of the coating substance to the bladder wall and provides continuous controlled release of the drug over the treatment period. The coating substance may be a mucoadhesive formulation, such as gels, ointments, creams, pastes, films, emulsion gels, tablets, polymers, or a combination thereof. Mucoadhesive formulation polymers may include hydrogels or hydrophilic polymers, polycarbophil (i.e. Carbopols, etc.), chitosan, polyvinylpyrrolidone (PVP), lectin, polyethyleneglycolated polymers, celluloses, or a combination thereof. Suitable celluloses include methyl cellulose (MC), carboxymethyl cellulose (CMC), hydroxypropyl cellulose (HPC), or combinations thereof. The coating substance may include a permeation enhancer. Non-limiting examples of permeation enhancers include dimethyl sulfoxide (DMSO), sodium carboxymethyl cellulose (NaCMC), lipids, surfactants, or combinations thereof. A coating substance may be deployed in the bladder so that the coating substance engages the bladder wall.

The coating substance may be deployed in the bladder using a deployment instrument. The deployment instrument may be any device designed to navigate natural lumens of the body to reach the intended implantation site. For deployment in the bladder, the deployment instrument is sized and shaped for passing through a urethra of a patient to a bladder. The deployment instrument may be a known device, such as a catheter or cystoscope, or a specially designed device. The deployment instrument is used to deploy the coating substance into the body and is subsequently removed from the body, leaving the coating substance wholly implanted in the body. Once so implanted, the coating substance may release drug into the body for an extended period. A comparable procedure can be used to deploy any of the devices or drugs described herein into other parts of the body through other natural lumens. For example, a deployment instrument can be used to deploy a liquid drug or drug formulation into the bladder by passing the deployment instrument through a urethra.

III. Exemplary Embodiments

Embodiment 1

A method of providing maintenance therapy for an individual, wherein the maintenance therapy follows at least one previous therapy, wherein the maintenance therapy comprises administering gemcitabine continuously to the individual two or more times during two or more delivery periods, wherein the gemcitabine is delivered locally to the bladder of the individual, wherein each delivery period is at least one week, wherein there is a rest period between each delivery period of at least one month, and wherein the individual has a urothelial carcinoma of the lower tract.

Embodiment 2

A method of maintenance therapy following at least one previous therapy for an individual having a urothelial carcinoma of the lower tract, comprising administering gemcitabine continuously and locally to the bladder of the individual two or more times during two or more delivery periods, wherein each delivery period is at least one week and there is a rest period between each delivery period of at least one month.

Embodiment 3

The embodiment of embodiment 1 or 2, wherein the gemcitabine is delivered into the bladder by an intravesicular device.

Embodiment 4

The method of embodiment 3, wherein the intravesicular device contains 225 mg gemcitabine.

Embodiment 5

The method of any of embodiments 1-4, wherein the delivery periods are each 3 weeks.

Embodiment 6

The method of any of embodiments 1-5, wherein the rest period is about 3 months.

Embodiment 7

The method of any of embodiments 1-6, wherein the gemcitabine is delivered at a dose from about 1 mg/day to about 300 mg/day during delivery periods.

Embodiment 8

The method any one of claims 1-7, wherein the concentration of gemcitabine in the urine is from about 1 µg/mL to about 10 µg/mL during the first and second delivery period.

Embodiment 9

The method of embodiment 8, wherein the concentration of gemcitabine in the urine is about 10 µg/mL during the delivery periods.

Embodiment 10

The method of any one of embodiments 1-9, wherein the individual is ineligible for or has refused cisplatin-based chemotherapy.

Embodiment 11

The method of any one of embodiments 1-10, wherein the individual is unfit for, ineligible for, or has refused a radical cystectomy.

Embodiment 12

The method of any one of embodiments 1-11, wherein the individual has muscle invasive bladder cancer.

Embodiment 13

The method of any one of embodiments 1-11, wherein the individual has non-muscle invasive bladder cancer.

Embodiment 14

The method of any one of embodiments 1-13, wherein the rest period between the delivery periods is about 3 months.

Embodiment 15

The method of any one of embodiments 1-14 comprising 4 delivery periods, wherein the rest period between each delivery period is about 3 months.

Embodiment 16

The method of any one of embodiments 1-14, wherein the rest period between each delivery period is about 3 months, and wherein the gemcitabine is delivered every 3 months for the lifetime of the individual.

Embodiment 17

A method of treating a urothelial carcinoma of the lower tract in an individual comprising a) administering to the individual continuously an effective amount of gemcitabine during an induction phase; and b) administering to the individual continuously an effective amount of gemcitabine during a maintenance phase, wherein the gemcitabine is delivered locally to the bladder of the individual, wherein the induction phase and maintenance phases are separated by a rest period, and wherein the induction phase is about 12 weeks.

Embodiment 18

A method of treating a urothelial carcinoma of the lower tract in an individual comprising a) administering to the individual an effective amount of gemcitabine continuously and locally to the bladder of the individual during an induction phase of about 12 weeks; and b) administering to the individual an effective amount of gemcitabine continuously and locally to the bladder of the individual during a maintenance phase, wherein the induction phase and maintenance phases are separated by a rest period.

Embodiment 19

A method of bladder preservation in an individual comprising: a) administering to the individual continuously an effective amount of gemcitabine during an induction phase; and b) administering to the individual continuously an effective amount of gemcitabine during a maintenance phase, wherein the gemcitabine is delivered locally to the bladder of the individual, wherein the induction phase and maintenance phases are separated by a rest period, wherein the induction phase is about 12 weeks, and wherein the individual has a urothelial carcinoma of the lower tract.

Embodiment 20

A method of bladder preservation in an individual having a urothelial carcinoma of the lower tract comprising: a) administering to the individual an effective amount of gemcitabine continuously and locally to the bladder of the individual during an induction phase of about 12 weeks; and b) administering to the individual an effective amount of gemcitabine continuously and locally to the bladder of the individual during a maintenance phase, wherein the induction phase and maintenance phases are separated by a rest period.

Embodiment 21

The method of any one of embodiments 17-20, wherein the gemcitabine is delivered by an intravesicular device.

Embodiment 22

The method of embodiment 21, wherein the intravesicular device contains 225 mg gemcitabine.

Embodiment 23

The method of any one of embodiments 17-22 wherein the rest period between the induction phase and the maintenance phase is about 3 months.

Embodiment 24

The method of any one of embodiments 17-23, wherein the maintenance phase comprises two or more gemcitabine delivery periods.

Embodiment 25

The method of embodiment 24, wherein the maintenance phase gemcitabine delivery periods are each separated by a rest period of about 3 months.

Embodiment 26

The method of any of embodiments 17-25, wherein the maintenance phase gemcitabine delivery periods are each 3 weeks.

Embodiment 27

The method of any of embodiments 24-26, wherein the gemcitabine is delivered at a dose from about 1 mg/day to about 300 mg/day during the induction phase or the maintenance phase delivery periods.

Embodiment 28

The method any one of embodiments 24-27, wherein the concentration of gemcitabine in the urine is from about 1 µg/mL to about 10 µg/mL during the induction phase or the maintenance phase delivery periods.

Embodiment 29

The method of any one of embodiments 17-28, wherein the individual is ineligible for or has refused cisplatin-based chemotherapy.

Embodiment 30

The method of any one of embodiments 17-29, wherein the individual is unfit for, ineligible for or has refused a radical cystectomy.

Embodiment 31

The method of any one of embodiments 17-30, wherein the individual has muscle invasive bladder cancer.

Embodiment 32

The method of any one of embodiments 17-30, wherein the individual has non-muscle invasive bladder cancer.

Embodiment 33

The method of any one of embodiments 1-32, wherein the individual is human.

EXAMPLES

Example 1

Subjects receive the first TAR-200 transuretherally via the TARTS Inserter on Study Day 0. On Study Day 21 (±3 days), this first TAR-200 will be removed via flexible or rigid cystoscopy, and then the second TAR-200 will be placed. TAR-200 is an intravesicular device that contains 225 mg of gemcitabine. This removal/replacement procedure is repeated for a third and fourth dosing cycle in the induction period on Study Days 42 (±3 days), and 63 (±3 days), respectively. The fourth TAR-200 will be removed on Study Day 84 (±3 days), and the 3-month response assessment will be conducted. See FIG. 1

During the maintenance period, a 21-day dosing cycle occurs every quarter (3 months) starting at approximately 6 months. Subjects may continue to undergo quarterly dosing cycles for 3 dosing cycles.

All subjects are assessed for clinical response every 3 months by cystoscopy, pelvic computed tomography (CT)/magnetic resonance imaging (MRI)/positron emission tomography (PET), and biopsy (at 12 weeks only, unless clinically indicated). Subjects are also assessed for symptom control at 3, 6, 9, and 12 weeks, and approximately every month during the maintenance period.

The primary endpoint is assessment of safety and tolerability of 4 consecutive 21 day TAR-200 dosing cycles.

The secondary endpoints are proportion of subjects with clinical complete response (cCR), clinical partial response (cPR), stable disease (SD), and progression on the basis of visual lesions on cystoscopy, pelvic CT/MRI/PET, and biopsy. For purposes of this study, cCR means no evidence of the disease in the bladder or notes. cPR means in the previously N0 subject, a down staging in bladder tumor burden to <pT2 disease and no evidence of nodal disease burden or in the N1-N3 subject: a down staging in bladder tumor burden to <pT2 disease and no evidence of an increase in the size of nodal disease burden or no evidence of down staging in bladder tumor burden and a decrease in the size of nodal disease burden. Stable disease means persistent MIBC without evidence of metastasis. Progression means M1 disease or significant increase in burden of disease in bladder based upon cystoscopy and Ct/MRI/PET. Symptom control, defined as changes in bladder-related symptoms per the protocol-specified bladder symptom and toxicity grading system. Other secondary endpoints are time to intervention for symptom control, defined as the time from the date of the first TAR-200 insertion to the date of intervention for symptom palliation; time to progression, defined as the time from the date of the first TAR-200 insertion to the date of the first occurrence of progression; proportion of subjects undergoing post-treatment interventions for the management of local symptoms by 3, 6, 9, and 12 months; and proportion of subjects surviving at 12 months.

To be eligible to participate in this study, subjects must meet all of the following inclusion criteria at the time of enrollment:

1. Histological proof of muscle-invasive urothelial cell carcinoma of the bladder (T2-T4a). Subjects with mixed histology are required to have dominant transitional cell pattern. Subjects with evidence of nodal disease below the aortic bifurcation may be included (cN0-cN3, M0).

2. Subject must have been as fully resected as possible per the physician's judgment.

3. Subjects must be deemed unfit for RC due to comorbid conditions with a risk of mortality due to RC ≥5% as estimated by the American College of Surgeons risk calculator using the current procedure terminology code 51595 or 51596 for cystectomy (http://riskcalculator.facs.org/RiskCalculator/PatientInfo.jsp).

4. Subjects must refuse cisplatin-based chemotherapy (and understand the risk and benefits of doing so) or be deemed ineligible for cisplatin-based chemotherapy by meeting at least one of the following criteria: World Health Organization (WHO) or Eastern Cooperative Oncology Group (ECOG) performance status of ≥2 or Karnofsky performance status of 60-70%, Creatinine clearance (calculated or measured) ≤60 mL/min, Common Terminology Criteria for Adverse Events (CTCAE) v4 Grade ≥2, audiometric hearing loss, CTCAE v4 Grade ≥2 peripheral neuropathy, New York Heart Association ≥Class III heart failure.

5. Life expectancy of at least 4 months.

6. Adequate bone marrow, liver, and renal function, as assessed by the following requirements conducted within 21 days prior to dosing: Hemoglobin ≥7.0 g/dL, Absolute neutrophil count (ANC) ≥1,500/mm3, Platelet count ≥75,000/mm3, Total bilirubin ≤2× the upper limit of normal (ULN), alanine aminotransferase (ALT) and aspartate aminotransferase (AST)≤3×ULN, Glomerular filtration rate ≥30% (≥30 ml/min/1.73 m2)

7. Subjects must be willing to undergo a cystoscopy for Investigational Product placement and removal.

Example 2

Twenty three patients were enrolled in the study as described in Example 1. The age range among the enrolled patients is from 50 to 98. The mean age is 82.6, and the median age is 84. The patients were treated and assessed according to the methods described therein. Patients that accomplished a complete response, partial response or stable disease after the induction phase received the maintenance phase treatment.

Results

Seven patients discontinued the study at some point during the induction due to various reasons. Out of the remaining sixteen patients, ten patients have completed the full four cycles of treatment during induction period. Five patients have completed the assessment at Day 180. The age range among the sixteen patients is from 50 to 98. The mean age is 81.75 and the median age is 84.

According to the evaluation at the end of the induction period (Day 84 of the study), a 50% complete response rate and a 80% objective response rate (ORR) was achieved on a per protocol basis. See Table 1. On an Intent-to-Treat (ITT) basis (including all the 23 enrolled patients), a 30% complete response rate and a 47% objective response rate was achieved. Four consecutive doses were well tolerated in all ten patients, and the evidence suggests a control of the symptoms and a durable effect at Day 180. Eight patients proceeded to the maintenance dosing.

TABLE 1

| Patient # | Age | Tumor Stage at Diagnosis | Histopathology (Biopsy) at D 84 | Whole-Body Imaging at D 84 | Response Assessment at D 84 | Day 180 Assessment |
|---|---|---|---|---|---|---|
| 1 | 96 | cT2 | Negative | NED | CR | NED |
| 2 | 84 | cT2 | Negative | NED | CR | N/A |
| 3 | 83 | cT2 | Negative | NED | CR | NED |
| 4 | 72 | cT2 | Negative | NED | CR | N/A |
| 5 | 77 | cT2 | Negative | NED | CR | N/A |

TABLE 1-continued

| Patient # | Age | Tumor Stage at Diagnosis | Histopathology (Biopsy) at D 84 | Whole-Body Imaging at D 84 | Response Assessment at D 84 | Day 180 Assessment |
|---|---|---|---|---|---|---|
| 6 | 88 | cT2 | Tis | NED | PR | N/A |
| 7 | 50 | cT2 | T1 | NED | PR | N/A |
| 8 | 85 | cT2 w/ Hydronephrosis | Negative | Stable Left Iliac Node | PR | Nodal Progression |
| 9 | 80 | cT2 w/ Hydronephrosis | Residual MIBC | NED | SD | NED |
| 10 | 98 | cT3 w/Trigonal Involvement | Residual MIBC | NED | SD | Progression/ Death at 6 mo |

NED: no evidence of disease.

Thirteen patients were assessed of the symptom of hematuria during the treatment. Four patients had a medical history of hematuria (including chronic hematuria, frank hematuria, occasional hematuria, or recurrent gross hematuria) had none or rare hematuria since Day 0. Patient #1 (previously with chronic hematuria), 5 (previously with occasional hematuria) and 9 (previously with recurrent gross hematuria) had no hematuria since Day 0. Especially, patient #1 had no hematuria for over 200 days.

TABLE 2

| Patent | Age | Med Hx | Day 0 | Day 21 | Day 42 | Day 63 | Day 84 | Day 120 | Day 150 | Day 180 | Day 201 |
|---|---|---|---|---|---|---|---|---|---|---|---|
| 1 | 96 | Chronic Hematuria | 0 | 0 | 0 | 0 | 0 | 0 | 0 | 0 | 0 |
| 2 | 85 | Frank Hematuria | 0 | 0 | 0 | 0 | 1 | ND | 0 | DC | DC |
| 3 | 98 | None | 0 | 0 | 0 | 0 | 0 | 0 | DC | DC | DC |
| 4 | 80 | None | 0 | 0 | 0 | 0 | 0 | TBD | TBD | TBD | TBD |
| 5 | 83 | Occasional Hematuria | 0 | 0 | 0 | 0 | 0 | TBD | TBD | TBD | TBD |
| 6 | 84 | None | 0 | 1 | 0 | 1 | 0 | TBD | TBD | TBD | TBD |
| 7 | 72 | None | 1 | 1 | ND | ND | ND | ND | TBD | TBD | TBD |
| 8 | 50 | None | 0 | 0 | 0 | 0 | TBD | TBD | TBD | TBD | TBD |
| 9 | 84 | recurrent gross hematuria | 0 | 0 | 0 | TBD | TBD | TBD | TBD | TBD | TBD |
| 10 | 77 | None | 0 | 0 | | TBD | TBD | TBD | TBD | TBD | TBD |
| 11 | 88 | None | | | 0 | 0 | TBD | TBD | TBD | TBD | TBD |
| 12 | 84 | None | | | | TBD | TBD | TBD | TBD | TBD | TBD |
| 13 | 86 | None | 0 | | TBD | TBD | TBD | TBD | TBD | TBD | TBD |

*TBD: to be determined; DC: discontinued; ND: not determined.

What is claimed is:

1. A method of providing maintenance therapy for an individual,
   wherein the maintenance therapy follows at least one previous therapy, wherein the maintenance therapy comprises
   administering gemcitabine continuously to the individual two or more times during two or more delivery periods
   wherein the gemcitabine is delivered locally to the bladder of the individual,
   wherein each delivery period is at least one week,
   wherein there is a rest period between each delivery period of at least one month, and
   wherein the individual has muscle invasive bladder cancer.

2. The method of claim 1, wherein the gemcitabine is delivered into the bladder by an intravesicular device.

3. The method of claim 2, wherein the intravesicular device contains about 225 mg gemcitabine.

4. The method of claim 1, wherein the delivery periods are each 3 weeks.

5. The method of claim 1, wherein the rest period is about 3 months.

6. The method of claim 1, wherein the gemcitabine is delivered at a dose from about 1 mg/day to about 300 mg/day during delivery periods.

7. The method of claim 1, wherein the concentration of gemcitabine in the urine is from about 1 μg/mL to about 10 μg/mL during the first and second delivery period.

8. The method of claim 7, wherein the concentration of gemcitabine in the urine is about 10 μg/mL during the delivery periods.

9. The method of claim 1, wherein the individual is ineligible for or has refused cisplatin-based chemotherapy.

10. The method of claim 1, wherein the individual is unfit for, ineligible for, or has refused a radical cystectomy.

11. The method of claim 1, wherein the rest period between the delivery periods is about 3 months.

12. The method of claim 1, comprising 4 delivery periods, wherein the rest period between each delivery period is about 3 months.

13. The method of claim 1, wherein the rest period between each delivery period is about 3 months, and wherein the gemcitabine is delivered about every 3 months for the lifetime of the individual.

14. A method of treating muscle invasive bladder cancer in an individual comprising
   a) administering to the individual continuously an effective amount of gemcitabine during an induction phase; and
   b) administering to the individual continuously an effective amount of gemcitabine during a maintenance phase, wherein the gemcitabine is delivered locally to the bladder of the individual, wherein the induction phase and maintenance phases are separated by a rest period, and wherein the induction phase is about 12 weeks.

15. A method of bladder preservation in an individual comprising
   a) administering to the individual continuously an effective amount of gemcitabine during an induction phase; and
   b) administering to the individual continuously an effective amount of gemcitabine during a maintenance phase, wherein the gemcitabine is delivered locally to the bladder of the individual, wherein the induction phase and maintenance phases are separated by a rest period, wherein the induction phase is about 12 weeks, and wherein the individual has muscle invasive bladder cancer.

16. The method of claim 14, wherein the gemcitabine is delivered by an intravesicular device.

17. The method of claim 16, wherein the intravesicular device contains about 225 mg gemcitabine.

18. The method of claim 14, wherein the rest period between the induction phase and the maintenance phase is about 3 months.

19. The method of claim 14, wherein the maintenance phase comprises two or more gemcitabine delivery periods.

20. The method of claim 19, wherein the maintenance phase gemcitabine delivery periods are each separated by a rest period of about 3 months.

21. The method of claim 14, wherein the maintenance phase gemcitabine delivery periods are each 3 weeks.

22. The method of claim 19, wherein the gemcitabine is delivered at a dose from about 1 mg/day to about 300 mg/day during the induction phase or the maintenance phase delivery periods.

23. The method of claim 19, wherein the concentration of gemcitabine in the urine is from about 1 µg/mL to about 10 µg/mL during the induction phase or the maintenance phase delivery periods.

24. The method of claim 14, wherein the individual is ineligible for or has refused cisplatin-based chemotherapy.

25. The method of claim 14, wherein the individual is unfit for, ineligible for or has refused a radical cystectomy.

* * * * *